US010736474B2

(12) United States Patent
Takaki et al.

(10) Patent No.: US 10,736,474 B2
(45) Date of Patent: Aug. 11, 2020

(54) TOILET SEAT DEVICE

(71) Applicant: TOTO LTD., Kitakyushu-shi, Fukuoka (JP)

(72) Inventors: Takeshi Takaki, Kitakyushu (JP); Hiroshi Tsuboi, Kitakyushu (JP); Hitoaki Higuchi, Kitakyushu (JP); Koji Sonoda, Kitakyushu (JP); Keisuke Tashiro, Kitakyushu (JP); Tomohiro Hara, Kitakyushu (JP); Yo Morotomi, Kitakyushu (JP)

(73) Assignee: TOTO LTD., Kitakyushu-Shi, Fukuoka (JP)

( * ) Notice: Subject to any disclaimer, the term of this patent is extended or adjusted under 35 U.S.C. 154(b) by 0 days.

(21) Appl. No.: 16/352,950

(22) Filed: Mar. 14, 2019

(65) Prior Publication Data
US 2019/0290079 A1  Sep. 26, 2019

(30) Foreign Application Priority Data

Mar. 23, 2018 (JP) ................... 2018-055711
Dec. 27, 2018 (JP) ................... 2018-245412

(51) Int. Cl.
*A47K 13/24* (2006.01)
*G01G 19/44* (2006.01)
*G01G 19/414* (2006.01)
*A61B 5/00* (2006.01)
*G01G 19/52* (2006.01)

(52) U.S. Cl.
CPC ............ *A47K 13/24* (2013.01); *A61B 5/4872* (2013.01); *G01G 19/414* (2013.01); *G01G 19/44* (2013.01); *G01G 19/52* (2013.01)

(58) Field of Classification Search
CPC .... A47K 13/14; A61B 5/4872; G01G 19/414; G01G 19/44; G01G 19/52
USPC ............................................................. 4/253
See application file for complete search history.

(56) References Cited

U.S. PATENT DOCUMENTS 4,697,656 A * 10/1987 de Canecaude ....... G01G 19/44
                                                177/144
9,867,513 B1 * 1/2018 Hall ....................... A47K 13/24
9,927,302 B1 * 3/2018 Hall ....................... G01G 19/44
(Continued)

OTHER PUBLICATIONS

English translation of JP2000-225101A dated Aug. 15, 2000, in the name of Matsushita Electric Ind. Co. Ltd.
(Continued)

*Primary Examiner* — Huyen D Le
(74) *Attorney, Agent, or Firm* — Pearne & Gordon LLP

(57) ABSTRACT

A toilet seat device includes a main part, a toilet seat, a load sensor, a controller, and a memory. The toilet seat includes a seating part where a user is seated, and a support leg part supporting a load applied to the seating part. The load sensor is provided in the support leg part and detects the load applied to the support leg part. The controller performs at least a body weight measurement of the user based on a detection result of the load sensor. The controller includes a register mode and a normal-use mode in the body weight measurement. The register mode includes determining an estimated value for estimating the total body weight of the user from the seated load. The normal-use mode includes estimating a load value relating to the total body weight of the user based on the estimated value.

16 Claims, 15 Drawing Sheets

(56) References Cited

U.S. PATENT DOCUMENTS

| | | | | |
|---|---|---|---|---|
| 2007/0061953 | A1* | 3/2007 | Rigas | A47K 13/24 |
| | | | | 4/242.1 |
| 2016/0374619 | A1* | 12/2016 | Borkholder | A61B 5/6891 |
| | | | | 600/301 |
| 2018/0271446 | A1* | 9/2018 | Zhou | A61B 5/6887 |
| 2019/0323880 | A1* | 10/2019 | Shimasaki | G01G 19/52 |

OTHER PUBLICATIONS

English translation of JPH09-119859A dated May 6, 1997, in the name of Matsushita Electric Ind. Co. Ltd.

English translation of JPH06-008548B2 dated Feb. 2, 1994 in the name of Aichi Electric Co. Ltd.

\* cited by examiner

TOILET SEAT DEVICE

CROSS-REFERENCE TO RELATED APPLICATIONS

This application is based upon and claims the benefit of priority from Japanese Patent Application No. 2018-055711, filed on Mar. 23, 2018 and Japanese Patent Application No. 2018-245412, filed on Dec. 27, 2018; the entire contents of which are incorporated herein by reference.

FIELD

Embodiments described herein relate generally to a toilet seat device.

BACKGROUND

Conventionally, a known toilet seat device can measure the body weight of a user by utilizing a toilet seat provided in an upper part of a sit-down flush toilet. Compared to a general body weight scale, the toilet seat device that can measure the body weight does not need storage space or the effort of obtaining the scale from the storage location and replacing it after each measurement is performed. Further, the sit-down flush toilet can perform daily body weight management continuously without conscious effort because the sit-down flush toilet is likely to be used daily by the user.

It is favorable to provide a load sensor at a support leg part of the toilet seat to be able to measure the body weight using a toilet seat device having a simple configuration (e.g., JP-A H6-8548 (Tokko)). To accurately measure the body weight of the user using the load sensor provided at the support leg part of the toilet seat, it is necessary for the total body weight of the user to be applied to the support leg part of the toilet seat. However, for the toilet seat device, for example, a foot of the user may undesirably touch the floor of the toilet room and cause the body weight of the user to be undesirably dispersed in the floor via the foot; therefore, the total body weight of the user is no longer applied to the toilet seat. Also, because the toilet seat is pivotally supported to be rotatable with respect to the main part, the body weight of the user may be dispersed through the rotation shaft part; and the total body weight of the user is no longer applied to the support leg part of the toilet seat.

Therefore, a toilet seat device is known in which the weight corresponding to the body weight applied to parts other than the toilet seat is predetermined by experiments, etc., before the body weight measurement; and the seated load that is measured by the toilet seat is increased by the weight corresponding to the body weight (e.g., JP-A H9-119859 (Kokai)).

However, the inventor of the application discovered that the body weight of the user dispersed in the floor of the toilet room and/or the rotation shaft part of the toilet seat changes greatly according to the physique, the sitting habits, etc., of the user; therefore, it is difficult to use the values determined by the experiments, etc., uniformly for all users.

SUMMARY

According to an embodiment of the invention, a toilet seat device is provided and includes a main part, a toilet seat pivotally supported to be rotatable with respect to the main part, a load sensor, a controller, and a memory; the toilet seat includes a seating part where a user is seated, and a support leg part supporting a load applied to the seating part; the load sensor is provided in the support leg part and detects the load applied to the support leg part; the controller performs at least a body weight measurement of the user based on a detection result of the load sensor; the controller includes a register mode and a normal-use mode in the body weight measurement; the register mode includes a first process of acquiring a first load value relating to a total body weight of the user, a second process of measuring a second load value relating to a seated load detected by the load sensor in a state in which the user is seated on the toilet seat, a third process of determining an estimated value for estimating the total body weight of the user from the seated load based on the first load value and the second load value and storing the estimated value in the memory; and the normal-use mode includes a fourth process of measuring a third load value relating to the seated load detected by the load sensor in the state in which the user is seated on the toilet seat, and a fifth process of estimating a fourth load value relating to the total body weight of the user based on the estimated value and the third load value.

DETAILED DESCRIPTION

Figure 1:
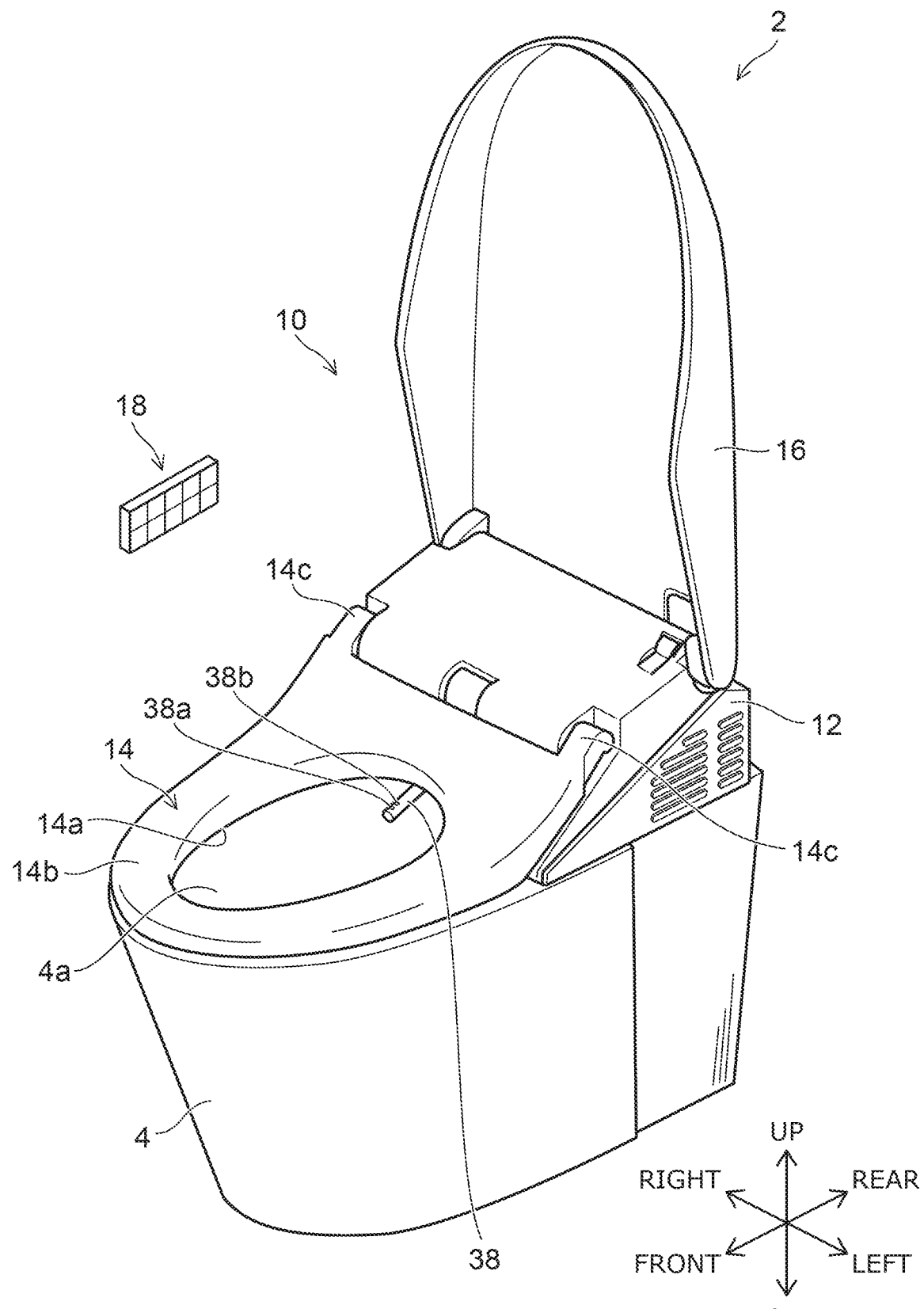
FIG. 1 is a perspective view schematically illustrating a toilet device including a toilet seat device according to a first embodiment.

A first invention is a toilet seat device including a main part, a toilet seat pivotally supported to be rotatable with respect to the main part, a load sensor, a controller, and a memory; the toilet seat includes a seating part where a user is seated, and a support leg part supporting a load applied to the seating part; the load sensor is provided in the support leg part and detects the load applied to the support leg part; the controller performs at least a body weight measurement of the user based on a detection result of the load sensor; the controller includes a register mode and a normal-use mode in the body weight measurement; the register mode includes a first process of acquiring a first load value relating to a total body weight of the user, a second process of measuring a second load value relating to a seated load detected by the load sensor in a state in which the user is seated on the toilet seat, a third process of determining an estimated value for estimating the total body weight of the user from the seated load based on the first load value and the second load value and storing the estimated value in the memory; and the normal-use mode includes a fourth process of measuring a third load value relating to the seated load detected by the load sensor in the state in which the user is seated on the toilet seat, and a fifth process of estimating a fourth load value relating to the total body weight of the user based on the estimated value and the third load value.

According to the toilet seat device, rather than using an estimated value for estimating the total body weight predetermined using general experimental values, the register mode includes determining and storing the estimated value based on the seated load and the total body weight of the user; therefore, the load that is dispersed in the floor and/or the rotation shaft part can be estimated by considering the physique and/or the sitting habits of the user; and a more accurate total body weight can be estimated.

A second invention is the toilet seat device of the first invention that further includes a posture measurement part measuring a seated posture of the user seated on the toilet seat, wherein the second process measures multiple second load values relating to the seated loads for each of multiple seated postures detected by the load sensor and the posture measurement part for a state in which the user is seated on the toilet seat and changes the seated posture; the third process determines, based on the first load value and the multiple second load values, multiple estimated values for estimating the total body weight of the user from the seated loads of each of the multiple seated postures and stores the multiple estimated values in the memory; the fourth process measures the seated posture detected by the posture measurement part and the third load value relating to the seated load detected by the load sensor in the state in which the user is seated on the toilet seat; and the fifth process estimates the fourth load value relating to the total body weight of the user based on the multiple estimated values, the third load value, and the seated posture measured in the fourth process.

According to the toilet seat device, the register mode includes determining and storing the estimated value for estimating the total body weight based on the total body weight and the seated loads of each of the seated postures of the user; therefore, by considering the seated posture of the user, the load that is dispersed in the floor and/or the rotation shaft part can be estimated; and a more accurate total body weight can be estimated.

A third invention is the toilet seat device of the second invention, wherein multiple load sensors are provided; and the posture measurement part measures the seated posture based on a load distribution of the multiple load sensors.

According to the toilet seat device, the configuration of the toilet seat device can be simplified because the seated posture can be measured using the load sensors provided to measure the body weight without providing a dedicated sensor for measuring the seated posture.

A fourth invention is the toilet seat device of the third invention, wherein at least one of the multiple load sensors is provided at a front of the toilet seat; an other at least one of the multiple load sensors is provided at a rear of the toilet seat; and the posture measurement part measures the seated posture according to a ratio of a detected value of the at least one of the load sensors provided at the front and a detected value of the other at least one of the load sensors provided at the rear.

According to the toilet seat device, a more accurate seated posture can be measured by the multiple load sensors.

A fifth invention is the toilet seat device of any one of the first to fourth inventions that further includes a user identifier identifying the user, wherein the controller performs an operation of the register mode each time the user is identified; the memory stores the estimated value each time the user is identified; and the controller uses the estimated value of each time the user is identified in the normal-use mode.

According to the toilet seat device, the estimated value is stored for each user utilizing the toilet seat device; therefore, the total body weights of the multiple users can be estimated accurately even when the physiques and/or the sitting styles are different between the users.

A sixth invention is the toilet seat device of any one of the first to fifth inventions, wherein the controller is configured to update the estimated value by re-performing an operation of the register mode after performing the operation of the register mode.

The estimated value that is used to estimate the total body weight of the user undesirably changes according to changes of the physique of the user. Therefore, there is a risk that the total body weight can no longer be estimated accurately using the estimated value stored previously in the case of a large physique change such as the growth of a child, dieting, gaining weight, etc. Conversely, according to the toilet seat device, because the estimated value can be updated, the total body weight can be estimated accurately by updating the estimated value even when a large physique change occurs.

A seventh invention is the toilet seat device of any one of the first to sixth inventions that further includes an operation part configured to command the controller to perform an operation of the register mode; and the controller is configured to perform the operation of the register mode at any timing corresponding to an operation of the operation part.

According to the toilet seat device, a more accurate estimated value of the total body weight can be obtained at the timing desired by the user by being able to perform the register mode at any timing. Also, the estimated value can be updated at the timing desired by the user; and the convenience of the toilet seat device can be improved.

An eighth invention is the toilet seat device of any one of the first to seventh inventions, wherein the controller automatically performs an operation of the register mode in the case where a prescribed condition is satisfied.

According to the toilet seat device, the estimated value can be updated to the newest value regularly; and the total body weight of the user can be measured more accurately. Also, the undesirable forgetting of the update of the estimated value can be suppressed appropriately.

A ninth invention is the toilet seat device of the seventh invention that further includes a notification part performing at least a prescribed notification, wherein the controller notifies, from the notification part in the case where a prescribed condition is satisfied, that the operation of the register mode is performed.

According to the toilet seat device, the estimated value can be updated to the newest value regularly; and the total body weight of the user can be measured more accurately. Also, the undesirable forgetting of the update of the estimated value can be suppressed appropriately.

A tenth invention is the toilet seat device of the eighth or ninth invention that further includes a timer measuring a time elapsed from performing the operation of the register mode; and in the case where the time measured by the timer is not less than a prescribed period of time, the controller determines that the prescribed condition is satisfied.

According to the toilet seat device, each time the prescribed period of time has elapsed, the estimated value can be updated or the user can be made aware of the need to update; and the total body weight of the user can be measured more accurately.

An eleventh invention is the toilet seat device of any one of the eighth to tenth inventions that further includes a counter counting a number of operations of the normal-use mode performed after the operation of the register mode is performed, wherein the controller determines that the prescribed condition is satisfied in the case where the number counted by the counter is not less than a prescribed number.

According to the toilet seat device, each time the user has utilized the toilet seat device the prescribed number of times, the estimated value can be updated or the user can be made aware of the need to update; and the total body weight of the user can be measured more accurately.

A twelfth invention is the toilet seat device of any one of the eighth to eleventh inventions, wherein the controller stores the first load value in the memory in the first process and determines that the prescribed condition is satisfied in the case where the fourth load value estimated in the normal-use mode is different from the first load value stored in the memory by not less than a prescribed value.

According to the toilet seat device, when the physique of the user has changed by the prescribed value or more, the estimated value can be updated or the user can be made aware of the need to update; and the total body weight of the user can be measured more accurately.

A thirteenth invention is the toilet seat device of any one of the first to twelfth inventions that further includes a notification part performing at least a prescribed notification, wherein the controller stores the fourth load value estimated in the normal-use mode in the memory, and performs a notification from the notification part in the case where the estimated fourth load value is different, by not less than a prescribed value, from the fourth load value of a previous time stored in the memory.

When the estimated value of the total body weight has changed greatly from the time of the previous time of use, there is a possibility that the total body weight of the user has not really changed; rather, the posture of the user may be drastically different from the posture when performing the register mode. Therefore, in the toilet seat device, a notification is performed from the notification part in the case where the estimated fourth load value is different from the fourth load value of the previous time stored in the memory by not less than the prescribed value. For example, a notification to correct the seated posture is performed, a notification of a measurement error is performed, or the user is prompted to re-measure. Thereby, a measurement error due to a change of posture, etc., can be suppressed; and the total body weight of the user can be measured more accurately.

Embodiments of the invention will now be described with reference to the drawings. Similar components in the drawings are marked with the same reference numerals; and a detailed description is omitted as appropriate.

First Embodiment

FIG. 1 is a perspective view schematically illustrating a toilet device including a toilet seat device according to a first embodiment.

As illustrated in FIG. 1, the toilet device 2 includes a sit-down flush toilet (for convenience of description hereinbelow, called simply the "toilet") 4 and a toilet seat device 10. The toilet seat device 10 is mounted at the upper part of the toilet 4. The toilet seat device 10 may be mounted integrally with the toilet 4 or may be detachably mounted to the toilet 4.

The toilet seat device 10 includes a main part 12, a toilet seat 14, and a toilet lid 16. The toilet lid 16 is provided as necessary in the toilet seat device 10 and is omissible. The toilet seat 14 and the toilet lid 16 are pivotally supported to be rotatable with respect to the main part 12.

In this specification, "up," "down," "front," "rear," "left," and "right" each are directions when viewed by the user sitting on the toilet seat 14 with the user's back facing the open toilet lid 16.

The toilet 4 includes a bowl 4a. The bowl 4a has a concave configuration that is concave downward. The toilet 4 receives, in the bowl 4a, excrement such as urine, feces, etc., of the user. The main part 12 of the toilet seat device 10 is mounted on a part of the toilet 4 rearward of the bowl 4a.

The toilet seat 14 for the user to be seated has an opening 14a exposing the bowl 4a. The toilet seat 14 is provided on the toilet 4 to surround the outer edge of the bowl 4a in the lowered state so that the bowl 4a is exposed via the opening 14a. Thereby, the user can excrete into the bowl 4a in the state of sitting on the toilet seat 14. In the example, a so-called O-shaped toilet seat 14 is shown in which the opening 14a is formed in a through-hole configuration. The toilet seat 14 is not limited to being O-shaped and may be U-shaped, etc. The opening 14a is not limited to a through-hole configuration and may have a notch configuration. The configuration of the toilet seat 14 when viewed from above in the state of use (the state in which the user can be seated) is a ring configuration or a U-shaped configuration.

The toilet seat 14 includes a seating part 14b. The seating part 14b is pivotally supported to be rotatable with respect to the main part 12 and is the part where the user is seated. The opening 14a is provided in the seating part 14b. In other words, the seating part 14b is O-shaped or U-shaped.

The seating part 14b includes a rotation shaft part 14c and is pivotally supported by the main part 12 to be rotatable via the rotation shaft part 14c. In other words, the rotation shaft part 14c is a hinge part. The seating part 14b includes, for example, a pair of rotation shaft parts 14c. The pair of rotation shaft parts 14c is provided at the two left/right direction-end parts at the rear end of the seating part 14b. A part of the main part 12 is inserted between the pair of rotation shaft parts 14c. Thereby, the pair of rotation shaft parts 14c and the part of the main part 12 between the pair of rotation shaft parts 14c are connected to be rotatable via the rotation shaft; and the seating part 14b (the toilet seat 14) is pivotally supported by the main part 12 to be rotatable.

Contrary to the description recited above, the seating part 14b (the toilet seat 14) may be pivotally supported by the main part 12 by providing one rotation shaft part 14c at the center vicinity of the rear end of the seating part 14b and by the one rotation shaft part 14c being inserted into the main part 12.

The toilet seat device 10 further includes a remote control 18. The remote control 18 includes, for example, multiple switches, sensors, etc., and receives operation commands from the user. The remote control 18 is connected to the main part 12 via a wired or wireless method and transmits the operation commands input from the user to the main part 12. The main part 12 performs the prescribed operations according to the operation commands input from the remote control 18. For example, the input of the operation commands to the main part 12 may be performed via an operation panel provided in the main part 12, etc. In other words, the remote control 18 is provided as necessary and is omissible.

Figure 2A:
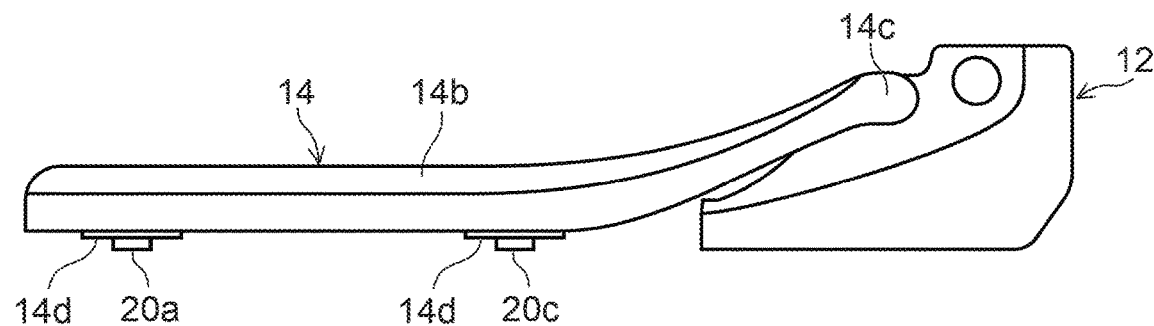
FIG. 2A and FIG. 2B are a side view and a bottom plan view schematically illustrating the toilet seat device according to the first embodiment.
Figure 2B:
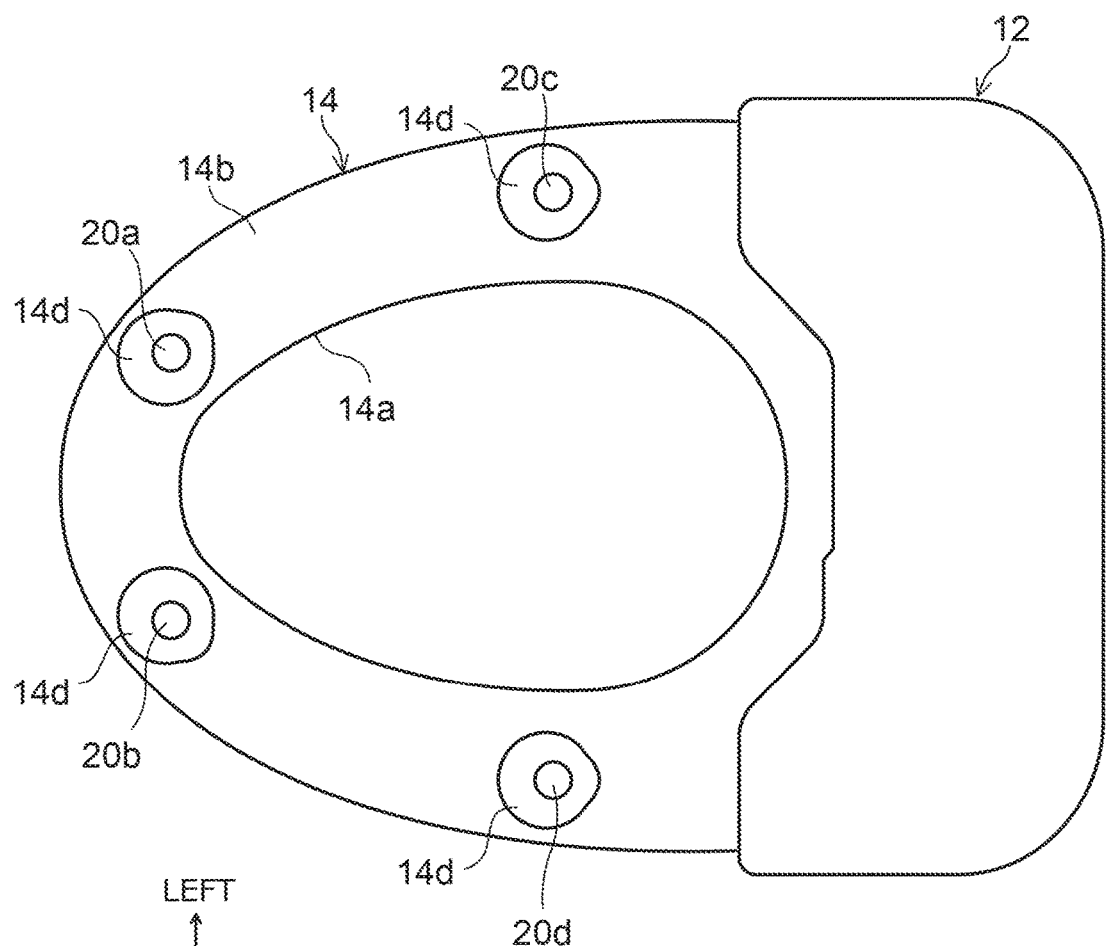

FIG. 2A and FIG. 2B are a side view and a bottom plan view schematically illustrating the toilet seat device according to the first embodiment.

As illustrated in FIG. 2A and FIG. 2B, the toilet seat 14 includes a support leg part 14d. The toilet seat device 10 further includes multiple load sensors 20a to 20d. The toilet lid 16 is not illustrated for convenience in FIG. 2A and FIG. 2B.

The support leg part 14d is provided at the bottom surface of the seating part 14b and supports a load applied to the seating part 14b. More specifically, the support leg part 14d supports the load applied to the seating part 14b when the user or the like is seated on the toilet seat 14 in the state in which the toilet seat 14 is lowered and placed on the toilet 4. The toilet seat 14 includes, for example, multiple support leg parts 14d.

The toilet seat 14 includes, for example, four support leg parts 14d. Two of the four support leg parts 14d are provided at the front of the toilet seat 14; and the remaining two support leg parts 14d are provided at the rear of the toilet seat 14. Thus, at least one of the multiple support leg parts 14d is provided at the front of the toilet seat 14; and an other at least one of the multiple support leg parts 14d is provided at the rear of the toilet seat 14. Although four support leg parts 14d are shown in the example, the number of the support leg parts 14d is not limited to four and may be any number. The number of the support leg parts 14d may be one.

The load sensors 20a to 20d are provided in the support leg parts 14d and detect the loads applied to the support leg parts 14d. The toilet seat device 10 measures the body weight of the user seated on the toilet seat 14 from the detected values of the load sensors 20a to 20d.

For example, the load sensors 20a to 20d detect the loads applied to the support leg parts 14d by being interposed between the upper surface of the toilet 4 and the support leg parts 14d of the toilet seat 14. The load sensors 20a to 20d include, for example, piezoelectric elements, strain gauges, etc. However, the configurations of the load sensors 20a to 20d are not limited to those recited above. The load sensors 20a to 20d may have any configuration that can detect the loads applied to the support leg parts 14d.

For example, the load sensors 20a to 20d are provided respectively at the four support leg parts 14d. The load sensors 20a and 20b are provided at the front of the toilet seat 14. The load sensors 20c and 20d are provided at the rear of the toilet seat 14. The front of the toilet seat 14 is, for example, a part frontward of the center of the frontward/rearward-direction length of the seating part 14b of the toilet seat 14 (a part other than the rotation shaft part 14c, etc.). In other words, the positions of the load sensors 20c and 20d are rearward of the load sensors 20a and 20b. The positions of the load sensors 20c and 20d may be any position rearward of the load sensors 20a and 20b.

Also, the load sensors 20a and 20c are provided at the left of the toilet seat 14; and the load sensors 20b and 20d are provided at the right of the toilet seat 14. For example, the load sensors 20a and 20b are provided at laterally-symmetric positions with the left/right-direction center of the toilet seat 14 interposed. Similarly, for example, the load sensors 20c and 20d are provided at laterally-symmetric positions with the left/right-direction center of the toilet seat 14 interposed.

However, the positions of the load sensors 20a to 20d are not limited to those recited above and may be any position where the loads applied to the support leg parts 14d can be detected appropriately. Also, the number of load sensors is not limited to four and may be any number that can appropriately detect the loads applied to the support leg parts 14d. The number of load sensors may be one. The number of load sensors may not be always be the same as the number of the support leg parts 14d. The number of load sensors may be more or less than the number of the support leg parts 14d.

Figure 3:
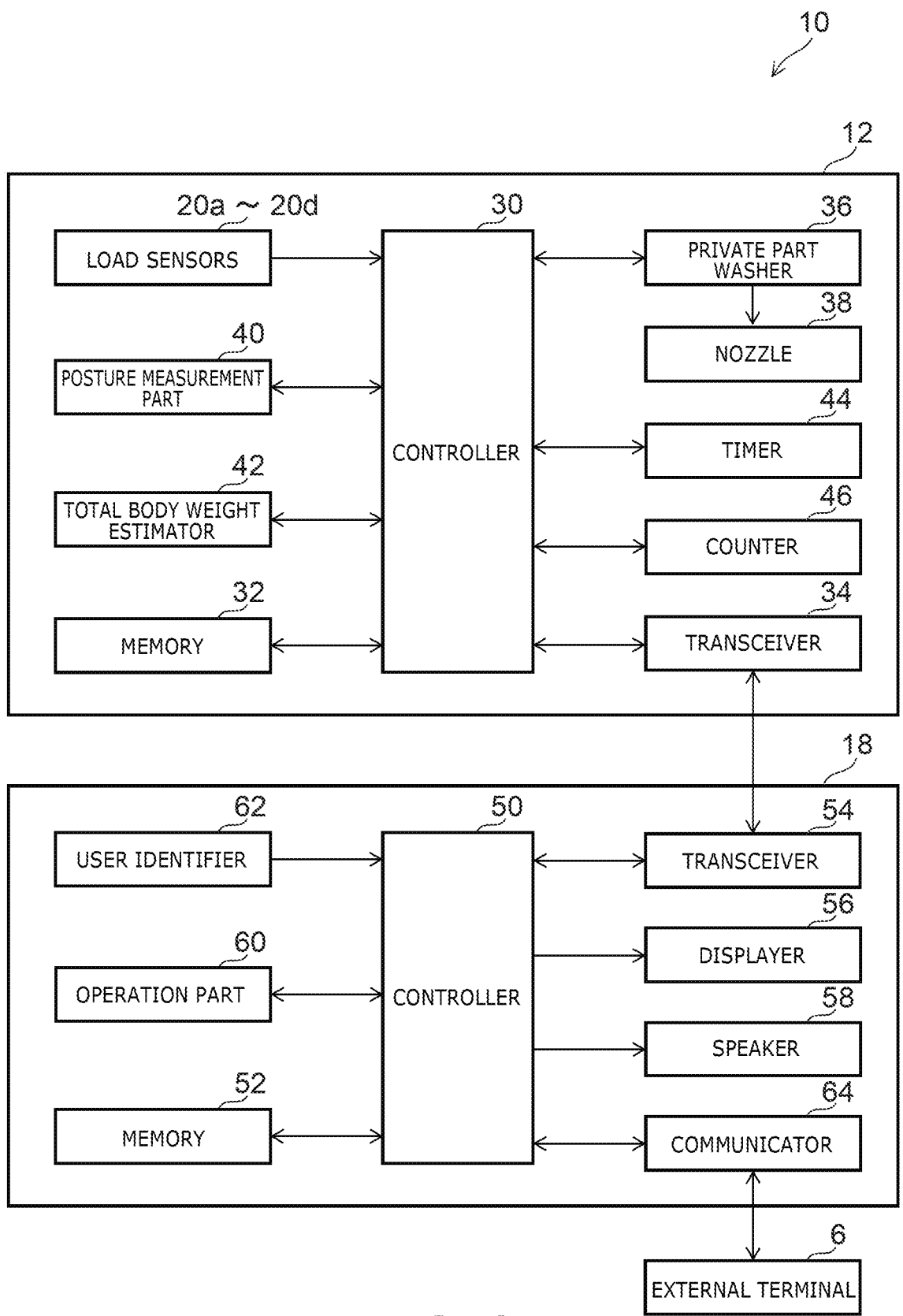
FIG. 3 is a block diagram schematically illustrating the toilet seat device according to the first embodiment.

FIG. 3 is a block diagram schematically illustrating the toilet seat device according to the first embodiment.

As illustrated in FIG. 3, the main part 12 of the toilet seat device 10 includes a controller 30, a memory 32, a transceiver 34, a private part washer 36, a nozzle 38, a posture measurement part 40, a total body weight estimator 42, a timer 44, and a counter 46. The remote control 18 of the toilet seat device 10 includes a controller 50, a memory 52, a transceiver 54, a displayer 56 (a notification part), a speaker 58 (a notification part), an operation part 60, a user identifier 62, and a communicator 64.

The controller 30 of the main part 12 comprehensively controls the operations of the parts of the toilet seat device 10. The memory 32 is connected to the controller 30. For example, the memory 32 stores the various programs, data, etc., necessary for the control of the controller 30. The controller 30 controls the parts of the toilet seat device 10 by reading the various programs, data, etc., from the memory 32. For example, the memory 32 may be included integrally in the controller 30.

Also, the controller 30 is connected to the load sensors 20a to 20d. The load sensors 20a to 20d input the detected values of the load to the controller 30. The controller 30 performs the body weight measurement of the user based on the detection results of the load sensors 20a to 20d. The memory 32 stores the result of the body weight measurement by the controller 30. For example, the memory 32 sequentially stores the information of the body weight of the user measured by the controller 30. Thereby, it is possible to manage the daily body weight change of the user, etc.

The controller 50 of the remote control 18 controls the operations of the parts of the remote control 18. The memory 52 is connected to the controller 50. The configurations of the controller 50 and the memory 52 can be similar to the configurations of the controller 30 and the memory 32. Accordingly, a detailed description is omitted for the controller 50 and the memory 52.

The transceiver 34 transceives signals between the transceiver 54 of the remote control 18. The transceiver 34 is connected to the controller 30. The transceiver 34 transmits the signals input from the controller 30 to the transceiver 54 of the remote control 18 and inputs the signals received from the transceiver 54 of the remote control 18 to the controller 30. Thereby, communication is possible between the main part 12 and the remote control 18 via the transceivers 34 and 54. The transceivers 34 and 54 may perform wireless communication or wired communication. In the case where it is unnecessary to transmit signals from the main part 12 to the remote control 18, a receiver may be provided in the main part 12 and a transmitter may be provided in the remote control 18 instead of the transceivers 34 and 54; and the signals may be transmitted only from the remote control 18 to the main part 12.

The displayer 56 and the speaker 58 that are provided in the remote control 18 are connected to the controller 50. The displayer 56 performs a prescribed display of a character, a pattern, an image, etc., based on the control of the controller 50. The displayer 56 includes, for example, any display device such as a liquid crystal display, etc. The speaker 58 outputs a prescribed voice based on the control of the controller 50. The displayer 56 performs a prescribed notification to the user, etc., by the display of a character, etc. Similarly, the speaker 58 performs a prescribed notification to the user, etc., by the output of a voice.

Thus, the displayer 56 and the speaker 58 function as a notification part performing prescribed notifications to the user, etc. However, the notification part is not limited to the displayer 56 and the speaker 58 and may be any member capable of the prescribed notification. Also, the notification part is not limited to the remote control 18 and may be provided in the main part 12, etc.

The operation part 60 is connected to the controller 50. The operation part 60 receives the operations of the user and inputs, to the controller 50, prescribed operation commands corresponding to the operations of the user. For example, the operation part 60 includes multiple operation members such as switches, sensors, etc., and inputs, to the controller 50, multiple operation commands corresponding to the operations of the operation members. The operation part 60 is not limited to the remote control 18 and may be provided in, for example, the main part 12, etc.

The private part washer 36 that is provided in the main part 12 washes a private part such as the "bottom" or the like of the user by discharging washing water toward the private part of the user. The private part washer 36 is connected to the nozzle 38. The nozzle 38 has water discharge ports 38a and 38b in the tip. For example, the private part washer 36 causes the nozzle 38 to advance and retract between a position stored inside the main part 12 and a position protruding frontward from the main part 12 and advanced into the bowl 4a. FIG. 1 illustrates the state in which the nozzle 38 is advanced into the bowl 4a.

The private part washer 36 washes the private part of the user by discharging washing water from the water discharge port 38a or the water discharge port 38b in the state in which the nozzle 38 is advanced into the bowl 4a. The water discharge port 38a is, for example, a bidet wash water discharge port washing a female private part of a woman sitting on the toilet seat 14. The water discharge port 38b is, for example, a bottom wash water discharge port washing the "bottom" of the user sitting on the toilet seat 14. In this specification, "water" includes not only cold water but also hot water that is heated.

The private part washer 36 is connected to the controller 30 and washes the private part of the user based on the control of the controller 30. For example, the controller 30 operates the private part washer 36 based on the operation commands input from the remote control 18. The operation part 60 of the remote control 18 includes, for example, an operation member for operating the operation of the private part washer 36 such as a wash button, a stop button, etc. When the operation commands for operating the private part washer 36 are input from the operation part 60, the controller 50 inputs the operation commands to the controller 30 of the main part 12 via the transceivers 34 and 54. The controller 30 controls the operation of the private part washer 36 according to the input operation commands. Thereby, the user can wash the private part according to the operation of the operation part 60 of the remote control 18.

The posture measurement part 40 measures the seated posture of the user seated on the toilet seat 14. The posture measurement part 40 is connected to the controller 30. Based on the control of the controller 30, the posture measurement part 40 measures the seated posture of the user and inputs the measured seated posture to the controller 30.

For example, the posture measurement part 40 measures the seated posture based on the detection results of the load sensors 20a to 20d input from the controller 30. For example, in the case where the detected values of the load sensors 20a and 20b at the front are greater than the detected values of the load sensors 20c and 20d at the rear, the posture measurement part 40 measures that the user has a forward-tilted seated posture. Conversely, in the case where the detected values of the load sensors 20c and 20d at the rear are greater than the detected values of the load sensors 20a and 20b at the front, it is measured that the user has a rearward-tilted seated posture. Also, for example, in the case where the detected values of the load sensors 20a and 20c at the left are greater than the detected values of the load sensors 20b and 20d at the right, the posture measurement part 40 measures that the user has a seated posture tilted to the left. Conversely, in the case where the detected values of the load sensors 20b and 20d at the right are greater than the detected values of the load sensors 20a and 20c at the left, it is measured that the user has a seated posture tilted to the right.

Thus, for example, the posture measurement part 40 measures the seated posture of the user seated on the toilet seat 14 using the ratio of the detected values of the load sensors 20a to 20d. However, the configuration of the posture measurement part 40 is not limited to that recited above. For example, the posture measurement part 40 may have a configuration in which the user is imaged using a camera, and the seated posture is measured by image processing, etc. The posture measurement part 40 may have any configuration that can measure the seated posture of the user seated on the toilet seat 14.

For example, when measuring the seated posture based on the detection results of the load sensors 20a to 20d, the posture measurement part 40 may be provided separately from the controller 30 as illustrated in FIG. 3 or may be included in the controller 30. In other words, the controller 30 may function as the posture measurement part 40. Also, for example, in the case where a camera or the like is used in the posture measurement part 40, the posture measurement part 40 is not limited to the main part 12 and may be provided in the remote control 18 or may be mounted to the wall surface of the toilet room, etc., separately from the main part 12 and/or the remote control 18. The posture measurement part 40 may be configured to be a body different from the main part 12 and/or the remote control 18 and may be connected to the main part 12 or the remote control 18 via a wired or wireless method, etc.

Also, the posture measurement part 40 is configured to measure whether or not the seated posture of the user is within a prescribed range. For example, when the detected values of the load sensors 20c and 20d provided at the rear are greater than the detected values of the load sensors 20a and 20b provided at the front, the posture measurement part 40 measures that the seated posture of the user is within the prescribed range. Then, for example, when the detected values of the load sensors 20c and 20d provided at the rear are not more than the detected values of the load sensors 20a and 20b provided at the front, the posture measurement part 40 measures that the seated posture of the user is outside the prescribed range. For example, the posture measurement part 40 also measures that the seated posture of the user is outside the prescribed range when the detected values of the load sensors 20c and 20d provided at the rear are larger than the detected values of the load sensors 20a and 20b provided at the front by a prescribed amount or more.

In other words, the posture measurement part 40 measures a rearward-tilted seated posture to be within the prescribed range, and measures a forward-tilted seated posture to be outside the prescribed range. The posture measurement part 40 also measures an excessively rearward-tilted seated posture to be outside the prescribed range. For example, an excessive tilt to the right, an excessive tilt to the left, etc., may be measured as being outside the prescribed range.

The posture measurement part 40 inputs, to the controller 30, the measurement results of whether or not the seated posture of the user is within the prescribed range. When the measurement of the posture measurement part 40 is within the prescribed range, the controller 30 uses at least one of the displayer 56 or the speaker 58 to notify the user to maintain the seated posture within the prescribed range.

By correcting the loads detected by the load sensors 20a to 20d, the total body weight estimator 42 estimates the total body weight of the user from the load (hereinbelow, called the seated load) in the state in which the user is seated on the toilet seat 14 with a foot touching the floor of the toilet room. At this time, the total body weight estimator 42 modifies the correction proportion based on the seated posture of the user measured by the posture measurement part 40.

For example, the total body weight estimator 42 estimates the total body weight of the user based on the loads detected by the load sensors 20a to 20d and the seated posture of the user measured by the posture measurement part 40 when the private part washer 36 is discharging water. However, the timing of the estimation of the total body weight of the user by the total body weight estimator 42 is not limited to that recited above and may be any timing.

For example, the total body weight estimator 42 is connected to the controller 30. The measurement result of the posture measurement part 40 is input from the controller 30 to the total body weight estimator 42; and the total body weight estimator 42 estimates the total body weight based on the control of the controller 30. Then, the total body weight estimator 42 inputs the estimated total body weight to the controller 30. The total body weight estimator 42 may be provided separately from the controller 30 as illustrated in FIG. 3 or may be included in the controller 30. In other words, the controller 30 may function as the total body weight estimator 42. In the case where the total body weight estimator 42 is provided separately from the controller 30, the total body weight estimator 42 is not limited to the main part 12 and may be provided in the remote control 18, etc.

The total body weight estimator 42 estimates the total body weight when the measurement by the posture measurement part 40 is within the prescribed range, and does not estimate the total body weight when the measurement by the posture measurement part 40 is outside the prescribed range. Then, when the measurement is within the prescribed range, the total body weight estimator 42 modifies the correction proportion according to the ratio of the detected values of the load sensors 20a and 20b provided at the front and the detected values of the load sensors 20c and 20d provided at the rear.

Figure 4A:
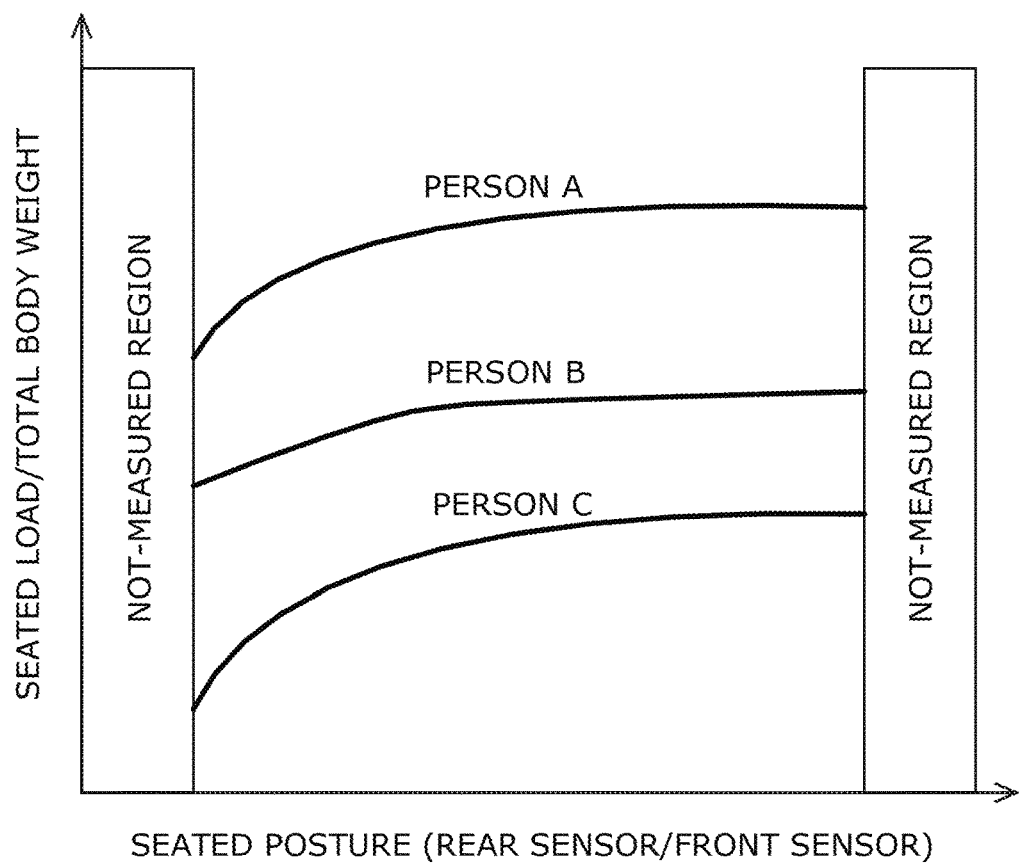
FIG. 4A and FIG. 4B are graphs schematically illustrating an example of characteristics of the seated load.
Figure 4B:
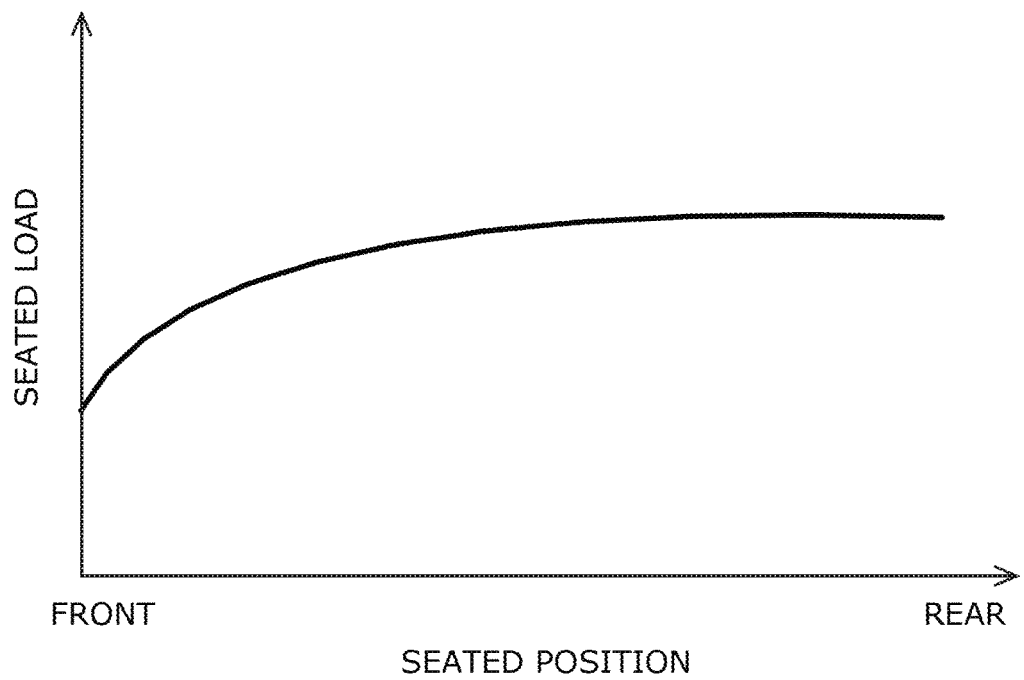

FIG. 4A and FIG. 4B are graphs schematically illustrating an example of characteristics of the seated load. As illustrated in FIG. 4A, when the ratio of the seated load to the total body weight is within the prescribed range, the ratio increases as the user becomes rearward-tilted. Also, the proportion of the change of the seated load increases as the user becomes forward-tilted. It is considered that this is because the ratio of the load applied to the floor, etc., increases when forward-tilted. On the other hand, the ratio of the seated load to the total body weight may again decrease when the user becomes excessively rearward-tilted due to the back of the user contacting the toilet lid 16, the tank provided at the rear, etc.

As illustrated in FIG. 4B, when the ratio of the seated load to the total body weight is within the prescribed range, the ratio increases as the seated position of the user moves to the rear. Accordingly, when the measurement is within the prescribed range, the total body weight estimator 42 modifies the correction proportion according to the ratio of the detected values of the load sensors 20a and 20b provided at the front and the detected values of the load sensors 20c and 20d provided at the rear.

For example, the total body weight estimator 42 stores a correction coefficient that decreases as the ratio of the detected values of the load sensors 20c and 20d provided at the rear increases. By multiplying the detected values of the load sensors 20a to 20d by the correction coefficient, the total body weight estimator 42 estimates the total body weight of the user while modifying the correction proportion based on the seated posture of the user. Or, the configuration may be such that a correction value that decreases as the ratio of the detected values of the load sensors 20c and 20d provided at the rear increases is stored; and the total body weight of the user is estimated by adding the correction value to the detected values of the load sensors 20a to 20d.

The controller 30 of the main part 12 includes a register mode and a normal-use mode in the body weight measurement. The register mode includes a first process, a second process, and a third process. The first process is a process of acquiring a first load value relating to the total body weight of the user. The second process is a process of measuring a second load value relating to the seated loads detected by the load sensors 20a to 20d in the state in which the user is seated on the toilet seat 14 with a foot touching the floor. The third process is a process of determining an estimated value for estimating the total body weight of the user from the seated load based on the first load value and the second load value and storing the estimated value in the memory 32.

The normal-use mode includes a fourth process and a fifth process. The fourth process is a process of measuring a third load value relating to the seated loads detected by the load sensors 20a to 20d in the state in which the user is seated on the toilet seat 14 with a foot touching the floor. The fifth process is a process of estimating a fourth load value relating to the total body weight of the user based on the estimated value and the third load value.

For example, in the normal-use mode, the controller 30 also stores the estimated fourth load value in the memory 32, and in the case where the estimated fourth load value is different from the fourth load value of a previous time stored in the memory 32 by not less than a prescribed value, performs a notification from at least one of the displayer 56 or the speaker 58.

The user identifier 62 that is provided in the remote control 18 identifies the user. For example, the user identifier 62 includes a selection member for selecting the designated user by the operations of the users such as a first user, a second user, etc. The selection member is by, for example, a button, a dial switch, etc. The user identifier 62 identifies the user based on the operation of the selection member by the user. For example, the user is identified to be the first user when the button of the first user is operated; and the user is identified to be the second user when the button of the second user is operated.

The user identifier 62 is connected to the controller 50. The user identifier 62 inputs the identification result of the user to the controller 50. When the identification result is input from the user identifier 62, the controller 50 inputs the identification result to the controller 30 of the main part 12 via the transceivers 34 and 54.

Based on the input identification result of the user, the controller 30 performs the operation of the register mode each time the user is identified. The memory 32 stores the estimated value each time the user is identified. Then, the controller 30 uses the estimated value in the normal-use mode each time the user is identified. Thereby, the body weight measurement can be performed for the different multiple users.

The configuration of the user identifier 62 is not limited to that recited above. For example, the user identifier 62 may have a configuration in which the user is imaged using a camera, and the user is identified by face authentication, etc. In such a case, the user identifier 62 may be provided in the main part 12 or may be provided separately from the main part 12 and the remote control 18. Or, the user identifier 62 may have a configuration in which the user is identified using the magnitude of the body weight, etc., based on the detected values of the load sensors 20a to 20d, etc. In such a case, the user identifier 62 may be included in the controller 30. In other words, the controller 30 may function as the user identifier. The user identifier 62 may have any configuration that can appropriately identify the multiple users. For example, in the case where a camera is used in each of the user identifier 62 and the posture measurement part 40, etc., these cameras may be used for more than one function. In other words, one camera may function as the user identifier 62 and the posture measurement part 40.

The controller 30 is configured to update the estimated value by re-performing the register mode operation after the register mode operation is performed. The operation part 60 includes, for example, an operation member for commanding the controller 30 to perform the register mode operation. For example, the controller 30 performs the register mode operation at any timing corresponding to an operation of a prescribed operation member of the operation part 60.

In the case where a prescribed condition is satisfied, the controller 30 automatically performs the register mode operation. Or, in the case where the prescribed condition is satisfied, the controller 30 notifies from at least one of the displayer 56 or the speaker 58 that the register mode operation is performed based on the operation of the operation part 60.

The timer 44 that is provided in the main part 12 measures the time elapsed from performing the register mode operation. For example, the timer 44 measures the time elapsed from performing the register mode operation for each of the multiple users. In the case where the time measured by the timer 44 is not less than a prescribed period of time, the controller 30 determines that the prescribed condition is satisfied, and performs the register mode operation or performs a notification of performing the register mode operation.

The counter 46 that is provided in the main part 12 counts the number of operations of the normal-use mode performed after the register mode operation is performed. For example, the counter 46 counts the number of operations of the normal-use mode for each of the multiple users. In the case where the number counted by the counter 46 is not less than a prescribed number, the controller 30 determines that the prescribed condition is satisfied, and performs the register mode operation or performs a notification of performing the register mode operation.

Also, in the first process, the controller 30 stores the first load value in the memory 32. Then, in the case where the fourth load value estimated in the normal-use mode is different from the first load value stored in the memory 32 by not less than the prescribed value, the controller 30 determines that the prescribed condition is satisfied, and performs the register mode operation or performs a notification of performing the register mode operation.

Thus, the controller 30 determines that the prescribed condition is satisfied when the prescribed period of time has elapsed from performing the register mode operation, when the normal-use mode has been performed a prescribed number of times after performing the register mode, and/or when the total body weight of the user has increased or decreased not less than a prescribed amount after performing the register mode. However, the prescribed condition is not limited to those recited above. The prescribed condition may be any condition for which it is necessary to re-perform the register mode operation and update the estimated value.

The communicator 64 that is provided in the remote control 18 is connected to an external terminal 6 via a wireless or wired method and communicates with the external terminal 6. By communicating with the external terminal 6 via the communicator 64, the toilet seat device 10 can acquire information of the total body weight of the user from the external terminal 6. The communicator 64 is connected to the controller 50. The controller 50 inputs the information of the total body weight input from the communicator 64 to the controller 30 of the main part 12 via the transceivers 34 and 54. The external terminal 6 is, for example, a smartphone of the user, a body weight scale including a communication function, a terminal mounted in a medical institution, etc. However, the external terminal 6 is not limited thereto and may be any terminal that can input the information of the total body weight of the user to the toilet seat device 10. Also, the communicator 64 is not limited to the remote control 18 and may be provided in the main part 12 or may be provided separately from the main part 12 and the remote control 18.

Figure 5:
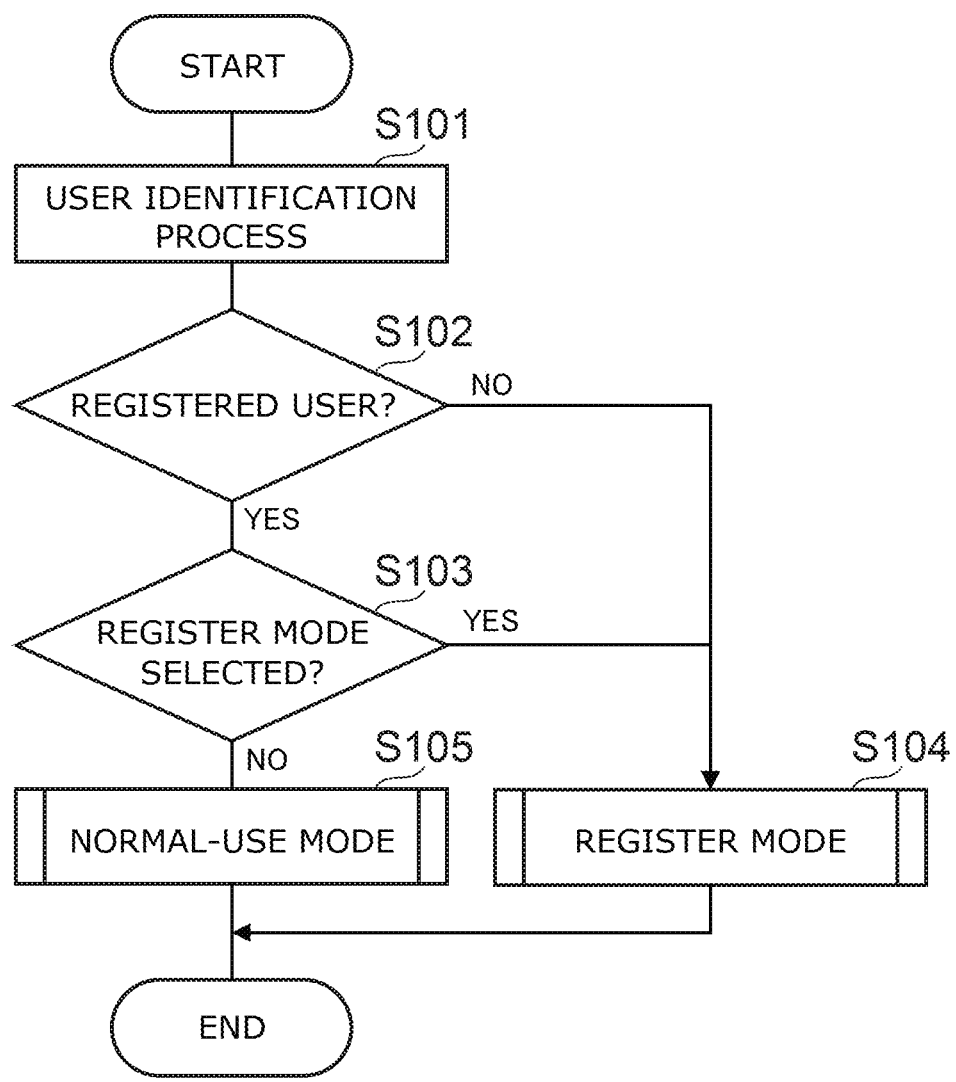
FIG. 5 is a flowchart schematically illustrating an example of an operation of the toilet seat device according to the first embodiment.

FIG. 5 is a flowchart schematically illustrating an example of an operation of the toilet seat device according to the first embodiment.

As illustrated in FIG. 5, when the toilet seat device 10 performs the body weight measurement of the user, first, a user identification process is performed (step S101 of FIG. 5). When the user desires the toilet seat device 10 to perform the body weight measurement, for example, the user operates the selection member provided in the user identifier 62 and selects himself or herself. Thereby, the user is identified by the user identifier 62; and the identification result is input to the controller 30. By, for example, using face authentication, etc., the user may be identified automatically when the user enters the toilet room, etc., without needing an operation of the user.

When the identification result of the user is input, the controller 30 determines whether or not the user is a registered user (step S102 of FIG. 5). In other words, the controller 30 determines whether or not an estimated value is stored in the memory 32 for the user.

In the case where the user is determined to be a registered user, continuing, the controller 30 determines whether or not the user has operated the operation part 60 to select the operation of the register mode (step S103 of FIG. 5). In the case where it is determined that the user is not registered or in the case where the user selects to perform the register mode operation, the controller 30 performs the register mode operation (step S104 of FIG. 5).

On the other hand, the controller 30 performs the operation of the normal-use mode in the case where the user is registered and the user has not selected to perform the register mode operation (step S105 of FIG. 5).

Figure 6:
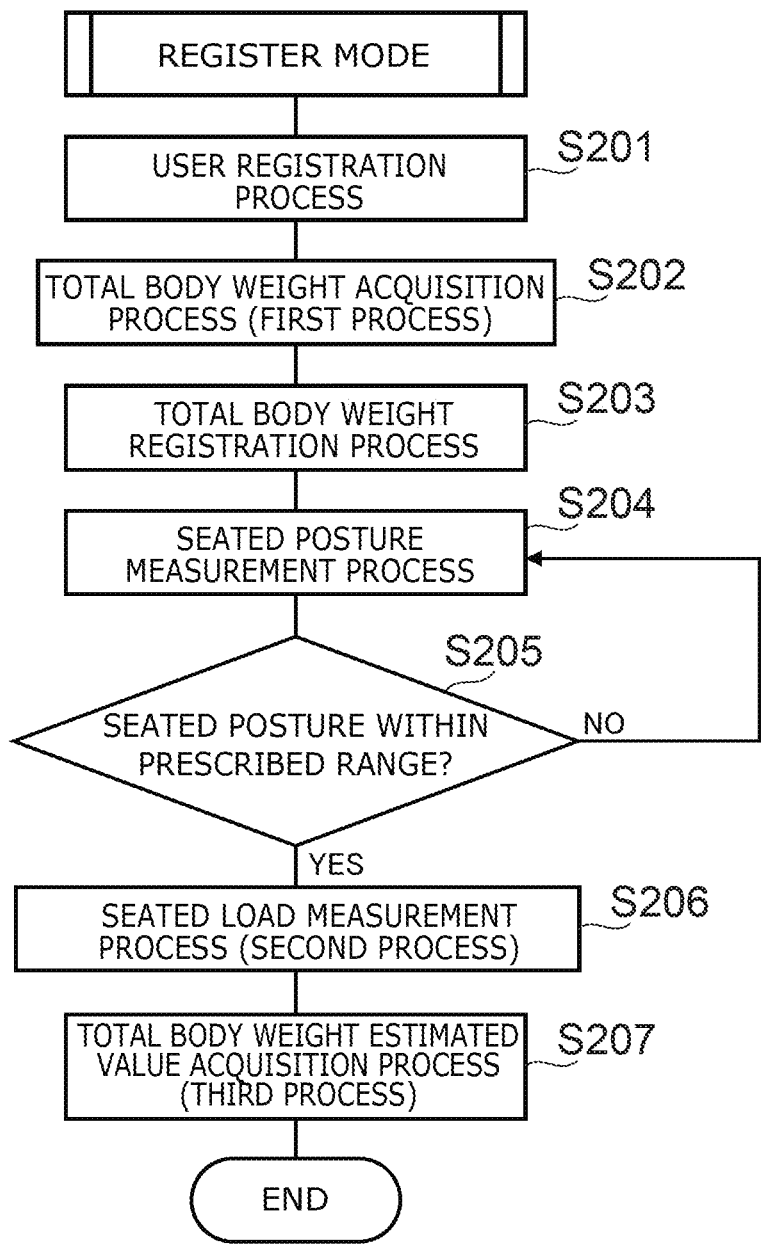
FIG. 6 is a flowchart schematically illustrating an example of the register mode operation of the toilet seat device according to the first embodiment.

FIG. 6 is a flowchart schematically illustrating an example of the register mode operation of the toilet seat device according to the first embodiment.

Figure 7A:
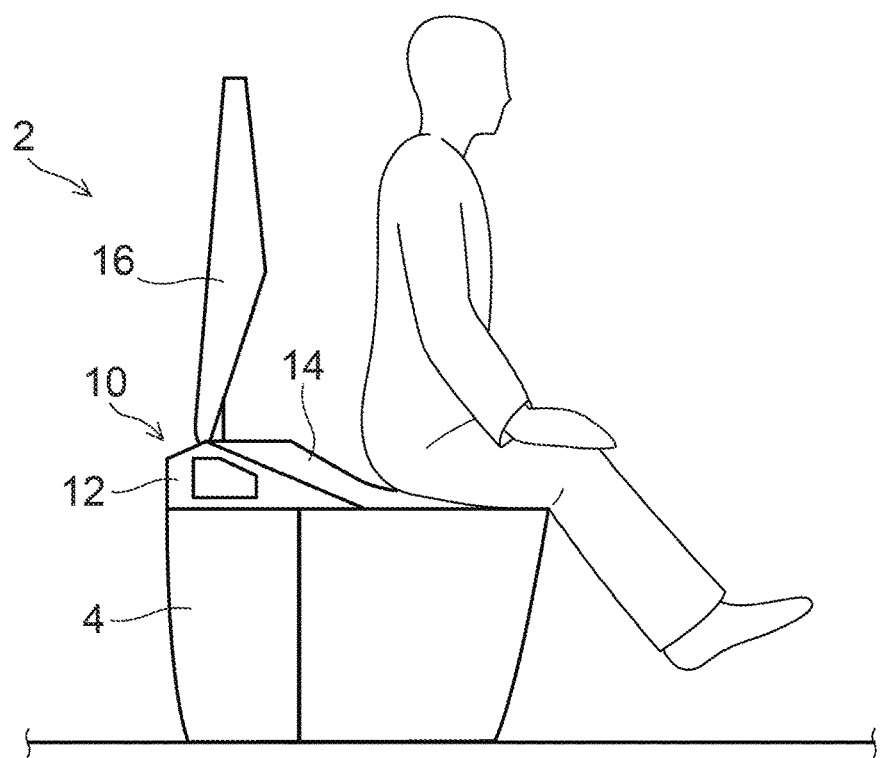
FIG. 7A and FIG. 7B are descriptive views schematically illustrating an example of operations of the user in the register mode.
Figure 7B:
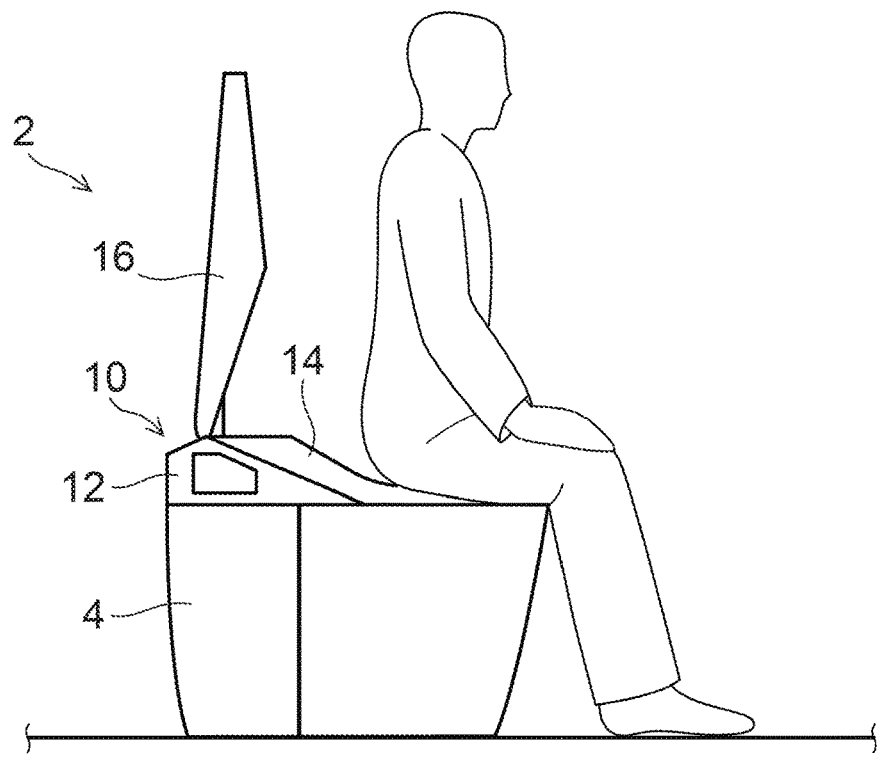

FIG. 7A and FIG. 7B are descriptive views schematically illustrating an example of operations of the user in the register mode.

As illustrated in FIG. 6, when the register mode operation is started, first, the controller 30 performs a user registration process (step S201 of FIG. 6). In the user registration process, for example, the user is registered by associating the user and the selection member of the user identifier 62. Or, in the case of face authentication, etc., the user is registered by associating the user and information of the face of the user. For example, the registered information is stored in the memory 32.

After the user is registered, the controller 30 performs a total body weight acquisition process (a first process) (step S202 of FIG. 6). In the total body weight acquisition process, for example, as illustrated in FIG. 7A, the user that is seated on the toilet seat 14 is caused to form a posture having the feet away from the floor. In other words, a posture that has the total body weight of the user applied to the toilet seat 14 is formed. For example, the controller 30 causes the user to form the posture recited above by notifying by at least one of the displayer 56 or the speaker 58. Then, the controller 30 acquires the first load value relating to the total body weight of the user by measuring the total body weight of the user from the detection results of the load sensors 20a to 20d in this state. After acquiring the first load value, the controller 30 causes the user seated on the toilet seat 14 to form a posture in which the feet touch the floor as illustrated in FIG. 7B by notifying by at least one of the displayer 56 or the speaker 58.

The first load value relating to the total body weight of the user is not limited to the measurement recited above and may be acquired by, for example, an input from the external terminal 6. Or, the first load value may be acquired by causing the user to input the information of the total body weight using an operation of the operation part 60.

After acquiring the first load value, the controller 30 performs a total body weight registration process (step S203 of FIG. 6). In the total body weight registration process, the controller 30 stores, in the memory 32, the first load value acquired in the total body weight acquisition process. Also, at this time, the controller 30 may notify the user by at least one of the displayer 56 or the speaker 58 that the first load value is acquired, that is, the total body weight is measured.

After storing the first load value in the memory 32, the controller 30 performs a seated posture measurement process (step S204 of FIG. 6). The controller 30 causes the posture measurement part 40 to measure the seated posture of the user seated on the toilet seat 14 with the feet touching the floor. Then, based on the measurement result of the posture measurement part 40, the controller 30 determines whether or not the seated posture of the user is within a prescribed range (step S205 of FIG. 6).

In the case where it is determined that the seated posture of the user is outside the prescribed range, the controller 30 repeats the measurement of the seated posture by the posture measurement part 40 and the determination of whether or not the seated posture is within the prescribed range. At this time, for example, the controller 30 uses at least one of the displayer 56 or the speaker 58 to notify the user to form a correct seated posture of being seated on the toilet seat 14 with the feet touching the floor and the spine straight as illustrated in FIG. 7B.

The controller 30 performs a seated load measurement process (a second process) when continuing to determine that the seated posture of the user is within the prescribed range (step S206 of FIG. 6). In the seated load measurement process, the controller 30 measures a second load value relating to the seated loads detected by the load sensors 20a to 20d in the state in which the user is seated on the toilet seat 14 with a foot touching the floor.

After measuring the second load value, the controller 30 performs a total body weight estimated value acquisition process (a third process) (step S207 of FIG. 6). In the total body weight estimated value acquisition process, the controller 30 determines an estimated value for estimating the total body weight of the user from the seated load based on the first load value and the second load value and stores the estimated value in the memory 32. For example, the controller 30 determines the value of the second load value subtracted from the first load value to be the estimated value. Thereby, in the normal-use mode recited below, it is possible to easily estimate the total body weight of the user from the seated load by adding the estimated value to the seated load. Thus, the controller 30 ends the register mode operation.

Figure 8:
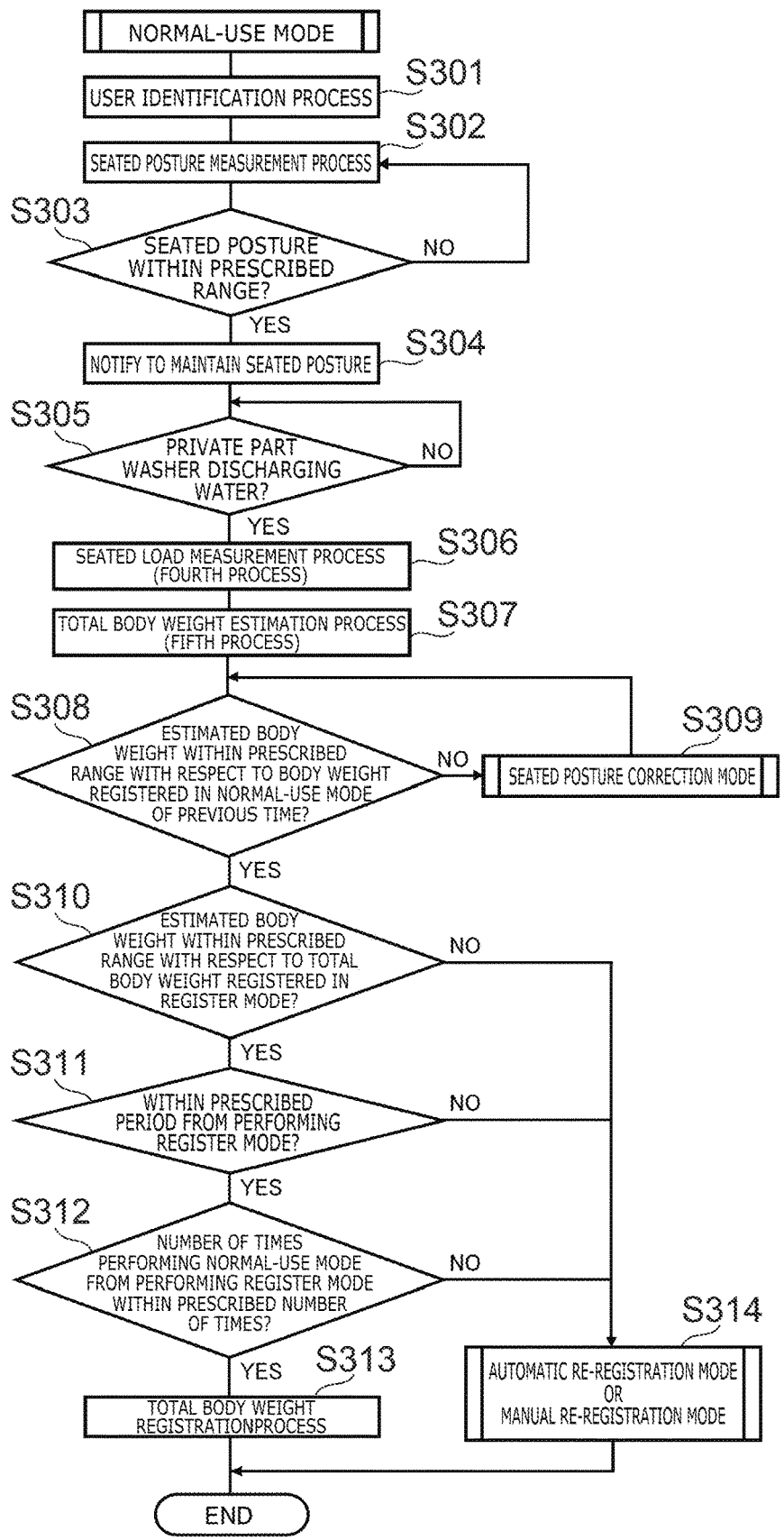
FIG. 8 is a flowchart schematically illustrating an example of the normal-use mode operation of the toilet seat device according to the first embodiment.

FIG. 8 is a flowchart schematically illustrating an example of the normal-use mode operation of the toilet seat device according to the first embodiment.

As illustrated in FIG. 8, when starting the normal-use mode operation, first, the controller 30 performs the user identification process (step S301 of FIG. 8). The controller 30 identifies the user based on the identification result input from the user identifier 62 and reads, from the memory 32, the estimated value of the identified user. In the normal-use mode, the controller 30 uses the estimated value of each time the user is identified.

The controller 30 identifies the user, reads the estimated value of the user, and subsequently performs the seated posture measurement process (step S302 of FIG. 8). In the normal-use mode, the user that is seated on the toilet seat 14 is caused to form a posture in which the feet touch the floor (referring to FIG. 7B). In the seated posture measurement process, the controller 30 causes the posture measurement part 40 to measure the seated posture of the user seated on the toilet seat 14 with the feet touching the floor. Then, based on the measurement result of the posture measurement part 40, the controller 30 determines whether or not the seated posture of the user is within the prescribed range (step S303 of FIG. 8).

In the case where it is determined that the seated posture of the user is outside the prescribed range, the controller 30 repeats the measurement of the seated posture by the posture measurement part 40 and the determination of whether or not the seated posture is within the prescribed range. At this time, for example, the controller 30 uses at least one of the displayer 56 or the speaker 58 to notify the user to form a correct seated posture of being seated on the toilet seat 14 with the feet touching the floor and the spine straight as illustrated in FIG. 7B.

In the case where it is determined that the seated posture of the user is within the prescribed range, the controller 30 uses at least one of the displayer 56 or the speaker 58 to notify the user to maintain the seated posture within the prescribed range (step S304 of FIG. 8).

After notifying the user to maintain the seated posture, the controller 30 determines whether or not the private part washer 36 is discharging water (step S305 of FIG. 8). In other words, the controller 30 determines whether or not an operation command for discharging washing water from the private part washer 36 (the nozzle 38) is input from the operation part 60.

In the case where it is determined that water discharge is being performed, the controller 30 responds by performing the seated load measurement process (the fourth process) (step S306 of FIG. 8). In the seated load measurement process, the controller 30 measures the third load value relating to the seated loads detected by the load sensors 20a to 20d in the state in which the user is seated on the toilet seat 14 with a foot touching the floor. Thus, the controller 30 detects the seated load using the load sensors 20a to 20d when the private part washer 36 is discharging water.

After measuring the third load value, the controller 30 performs a total body weight estimation process (a fifth process) (step S307 of FIG. 8). In the total body weight estimation process, the controller 30 causes the total body weight estimator 42 to estimate the total body weight of the user based on the third load value.

The total body weight estimator 42 estimates the total body weight of the user based on the third load value and the seated posture of the user measured by the posture measurement part 40. At this time, the total body weight estimator 42 modifies the correction proportion based on the seated posture of the user measured by the posture measurement part 40. In other words, the total body weight estimator 42 corrects the third load value based on the seated posture of the user. Subsequently, the controller 30 estimates the fourth load value relating to the total body weight of the user based on the estimated value and the third load value after correcting.

Thus, the controller 30 estimates the fourth load value relating to the total body weight of the user based on the estimated value acquired in the register mode while correcting the third load value based on the seated posture of the user measured by the posture measurement part 40. The total body weight of the user can be measured more accurately thereby.

After estimating the total body weight of the user, the controller 30 determines whether or not the estimated body weight is within a prescribed range with respect to the body weight (the first load value) registered in the register mode (step S308 of FIG. 8). In the case where the determination is outside the prescribed range, the controller 30 performs the operation of the seated posture correction mode (step S309 of FIG. 8).

In the case where the determination is within the prescribed range, the controller 30 continues to determine whether or not the estimated body weight (the fourth load value after correcting) is within a prescribed range with respect to the total body weight (the first load value) registered in the register mode (step S310 of FIG. 8).

In the case where the determination is within the prescribed range, the controller 30 continues to determine whether or not a prescribed period or less has elapsed from performing the register mode operation by referring to the timing of the timer 44 (step S311 of FIG. 8).

In the case where the determination is within the prescribed range, the controller 30 continues to determine whether or not the number of times the normal-use mode has been performed since performing the register mode operation is within a prescribed number of times by referring to the number of the counter 46 (step S312 of FIG. 8).

In the case where the determination is within the prescribed range, the controller 30 performs the total body weight registration process (step S313 of FIG. 8). In the total body weight registration process, the controller 30 stores the information of the estimated total body weight (the fourth load value after correcting) in the memory 32. Also, at this time, the controller 30 performs a notification of the acquired fourth load value, i.e., measured total body weight, to the user by at least one of the displayer 56 or the speaker 58.

On the other hand, in the case where the determination is outside the prescribed range in the processing of any of steps S310 to S312, the controller 30 performs the automatic re-registration mode operation or the manual re-registration mode operation (step S314 of FIG. 8). Thus, the controller 30 ends the normal-use mode operation.

It is sufficient to perform the automatic re-registration mode operation or perform the manual re-registration mode operation by an appropriate selection by, for example, an operation of the operation part 60, etc. Also, the processing of steps S310 to S312 is in no particular order and is interchangeable.

Figure 9:
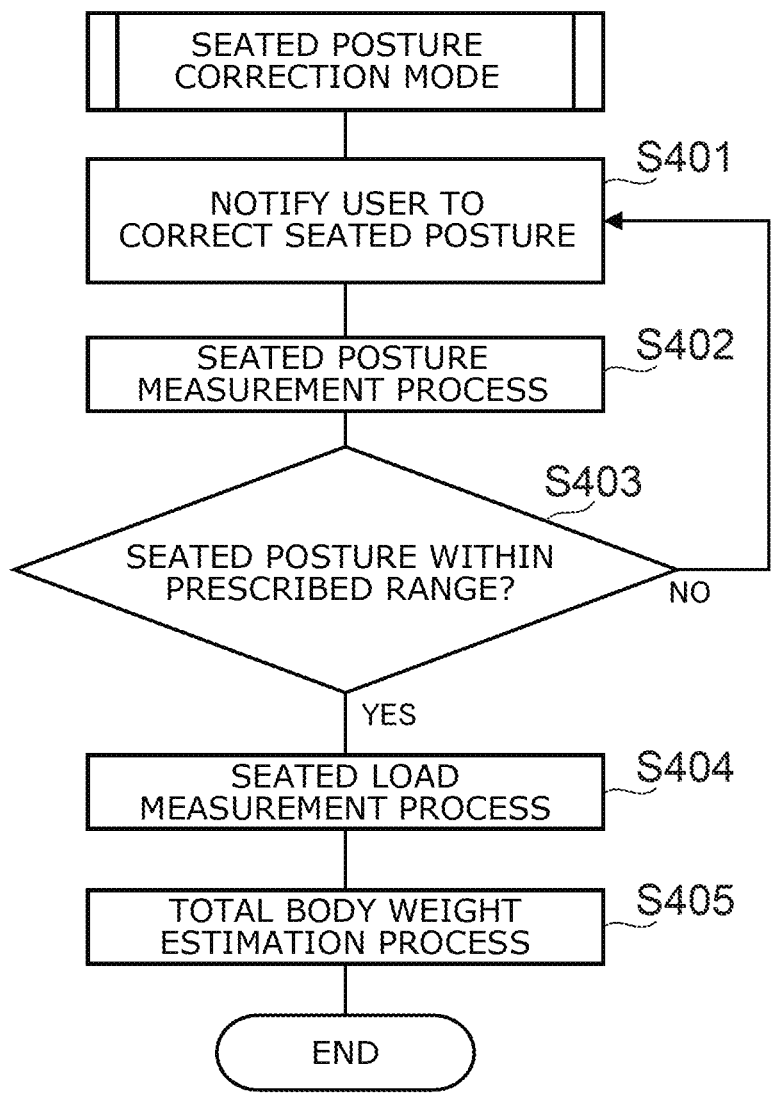
FIG. 9 is a flowchart schematically illustrating an example of the seated posture correction mode operation of the toilet seat device according to the first embodiment.

FIG. 9 is a flowchart schematically illustrating an example of the seated posture correction mode operation of the toilet seat device according to the first embodiment.

As illustrated in FIG. 9, when starting the seated posture correction mode operation, first, the controller 30 uses at least one of the displayer 56 or the speaker 58 to notify the user to correct the seated posture (step S401 of FIG. 9). Thus, the controller 30 stores the total body weight (the fourth load value) estimated in the normal-use mode in the memory 32, and performs a notification from the notification part of at least one of the displayer 56 or the speaker 58 in the case where the estimated total body weight is different from the fourth load value of a previous time stored in the memory 32 by not less than a prescribed value.

After performing the notification, the controller 30 performs the seated posture measurement process (step S402 of FIG. 9). In the seated posture measurement process, the controller 30 causes the posture measurement part 40 to measure the seated posture of the user seated on the toilet seat 14 with the feet touching the floor. Then, based on the measurement result of the posture measurement part 40, the controller 30 determines whether or not the seated posture of the user is within a prescribed range (step S403 of FIG. 9).

In the case where it is determined that the seated posture of the user is outside the prescribed range, the controller 30 performs a notification to correct the seated posture, and repeats the measurement of the seated posture by the posture measurement part 40 and the determination of whether or not the seated posture is within the prescribed range.

In the case where it is determined that the seated posture of the user is within the prescribed range, the controller 30 re-performs the operations of the seated load measurement process and the total body weight estimation process (steps S404 and S405 of FIG. 9). The operations of the seated load measurement process and the total body weight estimation process are substantially the same as the operations described in reference to steps S306 and S307 of FIG. 8; and a detailed description is therefore omitted. Thus, the controller 30 ends the seated posture correction mode operation.

Figure 10:
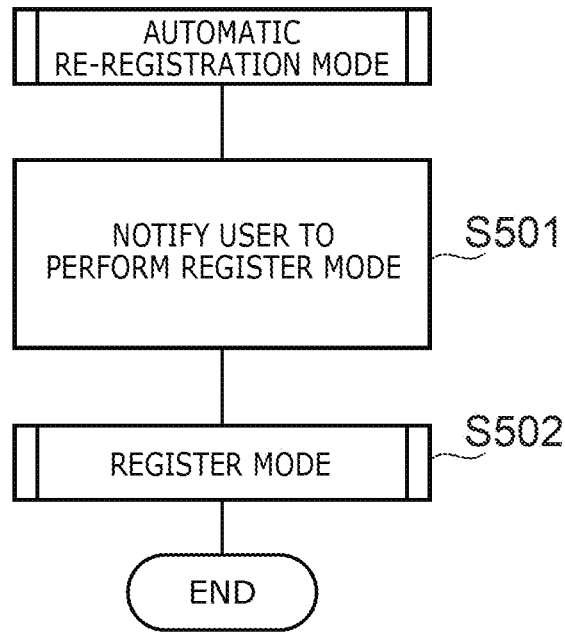
FIG. 10 is a flowchart schematically illustrating an example of the automatic re-registration mode operation of the toilet seat device according to the first embodiment.

FIG. 10 is a flowchart schematically illustrating an example of the automatic re-registration mode operation of the toilet seat device according to the first embodiment.

As illustrated in FIG. 10, when starting the automatic re-registration mode operation, first, the controller 30 uses at least one of the displayer 56 or the speaker 58 to notify the user that the register mode is performed (step S501 of FIG. 10). For example, the controller 30 notifies the user seated on the toilet seat 14 to form a posture having the feet away from the floor as illustrated in FIG. 7A.

After performing the notification, the controller 30 automatically performs the register mode operation (step S502 of FIG. 10). Thus, the controller 30 ends the automatic re-registration mode operation. Thus, in the case where the prescribed condition is satisfied, the controller 30 automatically performs the register mode operation. At this time, for example, the controller 30 may determine whether or not the user has formed a posture having the feet away from the floor based on the change of the detected values of the load sensors 20a to 20d, etc., and respond to the determination that the user has formed the posture having the feet away from the floor by automatically performing the register mode operation.

Figure 11:
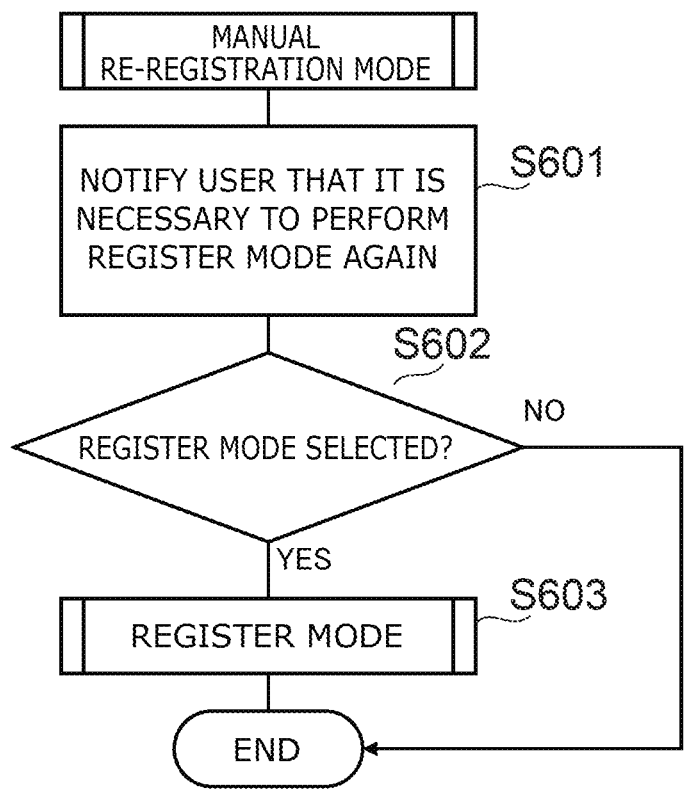
FIG. 11 is a flowchart schematically illustrating an example of the manual re-registration mode operation of the toilet seat device according to the first embodiment.

FIG. 11 is a flowchart schematically illustrating an example of the manual re-registration mode operation of the toilet seat device according to the first embodiment.

As illustrated in FIG. 11, when starting the manual re-registration mode operation, first, the controller 30 uses at least one of the displayer 56 or the speaker 58 to notify the user that it is necessary to re-perform the register mode (step S601 of FIG. 11).

After performing the notification, the controller 30 determines whether or not the user has selected the register mode operation from, for example, the operation of a prescribed operation member of the operation part 60 (step S602 of FIG. 11). Then, the controller 30 responds to the user selecting the register mode operation by performing the register mode operation (step S603 of FIG. 11). Thus, the controller 30 ends the manual re-registration mode operation. Thus, in the case where the prescribed condition is satisfied, the controller 30 notifies from the notification part of at least one of the displayer 56 or the speaker 58 that the register mode operation is performed.

As described above, the toilet seat device 10 according to the embodiment determines and stores the estimated value for estimating the total body weight in the register mode based on the seated load and the total body weight of the user rather than based on general predetermined experimental values; therefore, the accurate total body weight can be estimated by considering the physique and/or the sitting habits of the user in the state in which the feet touch the floor of the toilet room without the user raising his or her feet each time in the normal-use mode.

Also, in the toilet seat device 10, the estimated value is stored each time the user utilizes the toilet seat device 10; therefore, the total body weights of the multiple users can be estimated accurately even when the physiques and/or the sitting styles are different between the users.

The estimated value for estimating the total body weight of the user undesirably changes with changes of the physique of the user. Therefore, there is a risk that the total body weight can no longer be estimated accurately using the estimated value stored previously in the case of a large physique change such as the growth of a child, dieting, gaining weight, etc. Conversely, according to the toilet seat device 10, because the estimated value can be updated, the total body weight can be estimated accurately by updating the estimated value even when a large physique change occurs.

In the toilet seat device 10, a more accurate estimated value of the total body weight can be obtained at the timing desired by the user by being able to perform the register mode at any timing corresponding to the operation of the operation part 60. Also, the estimated value can be updated at the timing desired by the user; and the convenience of the toilet seat device 10 can be improved.

In the toilet seat device 10, the controller 30 automatically performs the register mode operation in the case where the prescribed condition is satisfied. Thereby, the estimated value can be updated to the newest value regularly; and the total body weight of the user can be measured more accurately. Also, the undesirable forgetting of the update of the estimated value can be suppressed appropriately.

In the toilet seat device 10, in the case where the prescribed condition is satisfied, the controller 30 performs a notification from the notification part of at least one of the displayer 56 or the speaker 58 that the register mode operation is performed. Thereby, the estimated value can be updated to the newest value regularly; and the total body weight of the user can be measured more accurately. Also, the undesirable forgetting of the update of the estimated value can be suppressed appropriately.

In the toilet seat device 10, in the case where the time that is measured by the timer 44 is not less than the prescribed period of time, the controller 30 determines that the prescribed condition is satisfied. Thereby, each time the prescribed period of time has elapsed, the estimated value can be updated or the user can be made aware of the need to update; and the total body weight of the user can be measured more accurately.

In the toilet seat device 10, in the case where the number counted by the counter 46 is not less than the prescribed number, the controller 30 determines that the prescribed condition is satisfied. Thereby, each time the user has utilized the toilet seat device 10 the prescribed number of times, the estimated value can be updated or the user can be made aware of the need to update; and the total body weight of the user can be measured more accurately.

In the toilet seat device 10, the controller 30 determines that the prescribed condition is satisfied in the case where the fourth load value estimated in the normal-use mode is different from the first load value stored in the memory 32 by not less than the prescribed value. Thereby, when the physique of the user has changed by the prescribed value or more, the estimated value can be updated or the user can be made aware of the need to update; and the total body weight of the user can be measured more accurately.

In the case where the estimated value of the total body weight has changed greatly from the time of the previous time of use, there is a possibility that the total body weight of the user has not really changed; and the posture of the user is drastically different from the posture when performing the register mode. Therefore, in the toilet seat device 10, a notification is performed from the notification part of at least one of the displayer 56 or the speaker 58 in the case where the estimated fourth load value is different from the fourth load value of a previous time stored in the memory 32 by not less than the prescribed value. For example, a notification to correct the seated posture is performed, a notification of a measurement error is performed, or the user is prompted to re-measure. Thereby, a measurement error due to a change of posture, etc., can be suppressed; and the total body weight of the user can be measured more accurately.

In the toilet seat device 10, the seated posture of the user is measured by the posture measurement part 40; and the total body weight estimator 42 corrects the loads detected by the load sensors 20a to 20d while considering the body weight of the user dispersed in the floor of the toilet room fluctuating according to the measured seated posture; therefore, the total body weight of the user can be estimated accurately.

As a result of continuing diligent research to accurately measure the total body weight, the inventor of the application discovered that the accurate body weight measurement cannot be performed for all postures in a toilet seat device 10 that measures the body weight from the load applied to the toilet seat 14. For example, when the seated posture of the user is an extreme rearward-tilted posture, the body weight of the user undesirably disperses not only in the floor of the toilet room but also in the hinge part of the toilet seat 14, etc. Also, when the seated posture of the user is an extreme forward-tilted posture, the proportion of the load dispersed in the floor undesirably increases. Further, when the user has a forward-tilted posture and grasps the handrail, etc., the body weight of the user undesirably disperses in the handrail as well. Conversely, in the toilet seat device 10, the estimation of the total body weight is performed only when the seated posture of the user is within the prescribed range. The total body weight of the user can be measured more accurately thereby.

As a result of many trials, the inventor of the application discovered that the posture suited to accurately estimating the total body weight is when much of the load is in a direction perpendicular to the load sensors 20a to 20d. More specifically, it was discovered that this posture is when seated with the spine properly straight. For such a posture, the seated load from the bottom through the back to the head is applied to the load sensors 20c and 20d provided at the rear; and the seated load of the thighs is applied to the load sensors 20a and 20b provided at the front; therefore, the detected values of the load sensors 20c and 20d provided rearward of the toilet seat 14 are greater than the detected values of the load sensors 20a and 20b provided at the front. Therefore, in the toilet seat device 10, the seated load that is used to estimate the total body weight of the user is the seated load when the measured seated posture is such that the detected values of the load sensors 20c and 20d provided at the rear are greater than the detected values of the load sensors 20a and 20b provided at the front. A more accurate body weight measurement can be performed thereby.

In the toilet seat device 10, it can be determined that the user has a posture tilted frontward or rearward according to the ratio of the detected values of the load sensors 20a to 20d provided at the front and rear. Then, a more accurate body weight measurement can be performed by modifying the correction proportion of the load when estimating the total body weight according to the tilt of the posture.

To perform the accurate body weight measurement, it is necessary for the user to maintain the seated posture within the prescribed range over a prescribed period. The toilet seat device 10 includes the notification part (the displayer 56 and/or the speaker 58) which notifies the user to maintain the seated posture within the prescribed range when measuring that the posture measurement part 40 is within the prescribed range; thereby, the user is prompted to maintain the seated posture; and a more accurate body weight measurement can be performed.

As a result of many trials, the inventor of the application discovered that not only the seated posture but also the seated position is important to measure the total body weight. Then, the inventor of the application discovered that although it is difficult to be seated by conscious effort at the same position each time, the user matches the position of the private part with the position of the washing water discharged from the private part washer 36 when using the private part washer 36 and therefore is seated at substantially the same position. In the toilet seat device 10, the total body weight of the user is estimated based on the loads detected by the load sensors 20a to 20d and the seated posture of the user measured by the posture measurement part 40 when the private part washer 36 is discharging water. Thereby, the shift of the seated position of the user can be suppressed; and a more accurate body weight measurement can be performed.

In the embodiment recited above, the seated load measurement process (the fourth process) is performed when the private part washer 36 is discharging water in the normal-use mode. This is not limited thereto; for example, the seated load measurement process may be performed by responding to the determination that the seated posture of the user is within the prescribed range.

Also, in the embodiment recited above, the total body weight estimation process (the fifth process) estimates the total body weight of the user by estimating the fourth load value relating to the total body weight of the user based on the command value acquired in the register mode and by further correcting the fourth load value based on the seated posture of the user measured by the posture measurement part 40. The estimate of the total body weight is not limited thereto and may be only the estimation based on the command value and the third load value or may be only the estimation based on the correction of the seated load by the total body weight estimator 42.

Second Embodiment

Figure 12:
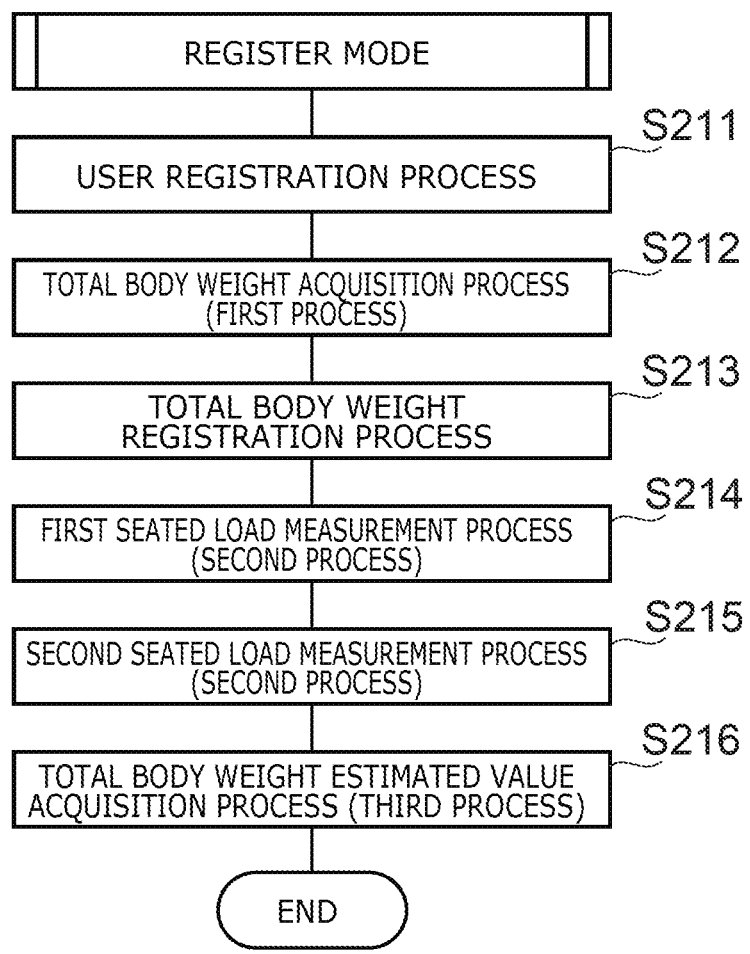
FIG. 12 is a flowchart schematically illustrating an example of a register mode operation of a toilet seat device according to a second embodiment.

FIG. 12 is a flowchart schematically illustrating an example of a register mode operation of a toilet seat device according to a second embodiment.

Figure 13A:
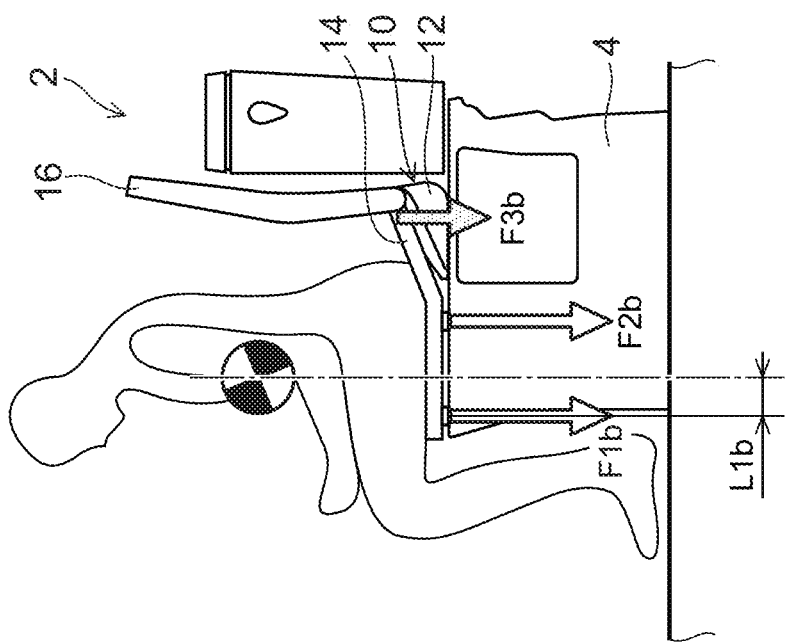
FIG. 13A to FIG. 13C are descriptive views schematically illustrating an example of operations of the user in the register mode.
Figure 13B:
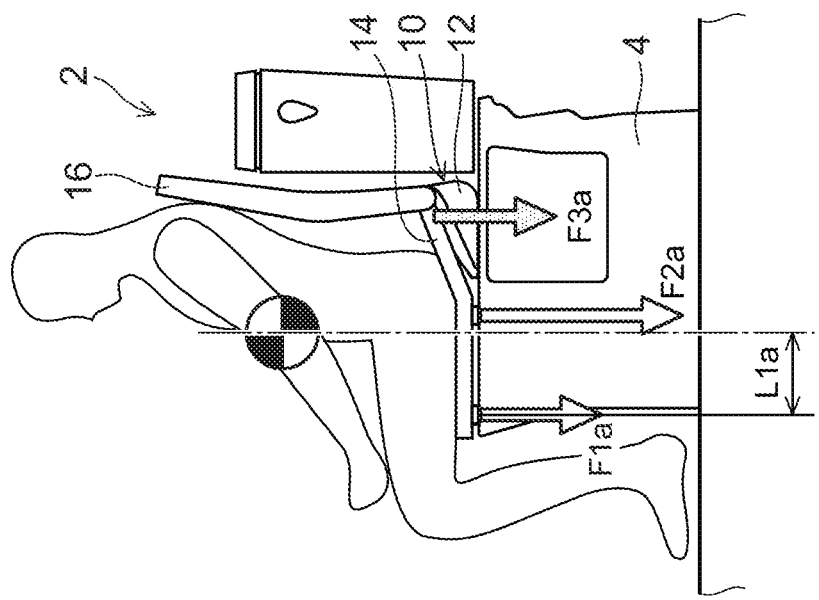
Figure 13C:
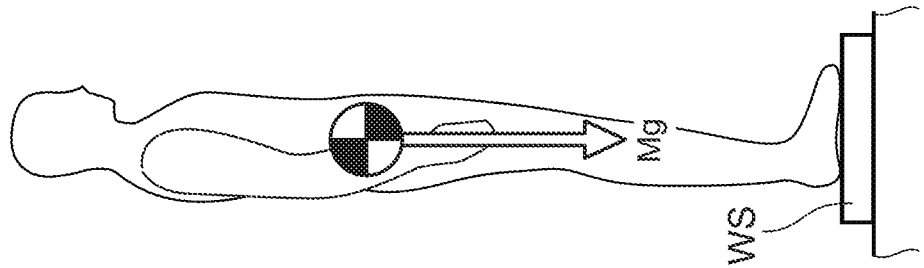

FIG. 13A to FIG. 13C are descriptive views schematically illustrating an example of operations of the user in the register mode.

As illustrated in FIG. 12, when starting the register mode operation, first, the controller 30 performs the user registration process (step S211 of FIG. 12). In the user registration process, for example, the user is registered by associating the user and the selection member of the user identifier 62. Or, in the case of face authentication, etc., the user is registered by associating the user and information of the face of the user. For example, the registered information is stored in the memory 32.

After registering the user, the controller 30 performs the total body weight acquisition process (the first process) (step S212 of FIG. 12). In the total body weight acquisition process, for example, the user uses the external terminal 6 or the operation part 60 of the remote control 18 to input the information of the total body weight after measuring the total body weight using a body weight scale WS, etc., as illustrated in FIG. 13A.

Thereby, the controller 30 acquires the first load value relating to the total body weight of the user based on the input from the external terminal 6 or the operation part 60. For example, by using the body weight scale WS including a communication function as the external terminal 6, the information of the total body weight may be input automatically to the controller 30 according to the measurement of the total body weight by the body weight scale WS.

After acquiring the first load value, the controller 30 performs the total body weight registration process (step S213 of FIG. 12). In the total body weight registration process, the controller 30 stores, in the memory 32, the first load value acquired in the total body weight acquisition process.

After storing the first load value in the memory 32, the controller 30 performs the first seated load measurement process (the second process) (step S214 of FIG. 12). In the first seated load measurement process, for example, the user that is seated on the toilet seat 14 is caused to form a first seated posture with the feet away from the floor as illustrated in FIG. 13B.

For example, the first seated posture is a rearward-tilted posture tilted rearward as illustrated in FIG. 13B. In other words, the first seated posture is a foot-raised rearward-tilted posture. For example, the controller 30 causes the user to form the first seated posture recited above by notifying by at least one of the displayer 56 or the speaker 58. Then, the controller 30 measures the second load value relating to the seated loads detected by the load sensors 20a to 20d in this state and causes the posture measurement part 40 to measure the first seated posture of the user.

After measuring the second load value of the first seated posture, the controller 30 performs a second seated load measurement process (the second process) (step S215 of FIG. 12). In the second seated load measurement process, for example, the user that is seated on the toilet seat 14 is caused to form a second seated posture with the feet away from the floor as illustrated in FIG. 13C.

The second seated posture is different from the first seated posture. For example, the second seated posture is a forward-tilted posture tilted frontward as illustrated in FIG. 13C. In other words, the second seated posture is a foot-raised forward-tilted posture. Contrary to the description recited above, the first seated posture may be a foot-raised forward-tilted posture; and the second seated posture may be a foot-raised rearward-tilted posture.

For example, the controller 30 causes the user to form the second seated posture recited above by notifying by at least one of the displayer 56 or the speaker 58. Then, the controller 30 measures the second load value relating to the seated loads detected by the load sensors 20a to 20d in this state and causes the posture measurement part 40 to measure the second seated posture of the user.

Thus, in the example, the second process measures multiple second load values relating to the seated loads for each of multiple seated postures detected by the posture measurement part 40 and the load sensors 20a to 20d in states in which the user is seated on the toilet seat 14 and changes the seated posture.

After measuring the multiple second load values, the controller 30 performs the total body weight estimated value acquisition process (the third process) (step S216 of FIG. 12). In the total body weight estimated value acquisition process, the controller 30 determines multiple estimated values for estimating the total body weight of the user from the seated loads for each of multiple seated postures based on the first load value and the multiple second load values, and stores the multiple estimated values in the memory 32. Thus, the controller 30 ends the register mode operation.

Figure 14:
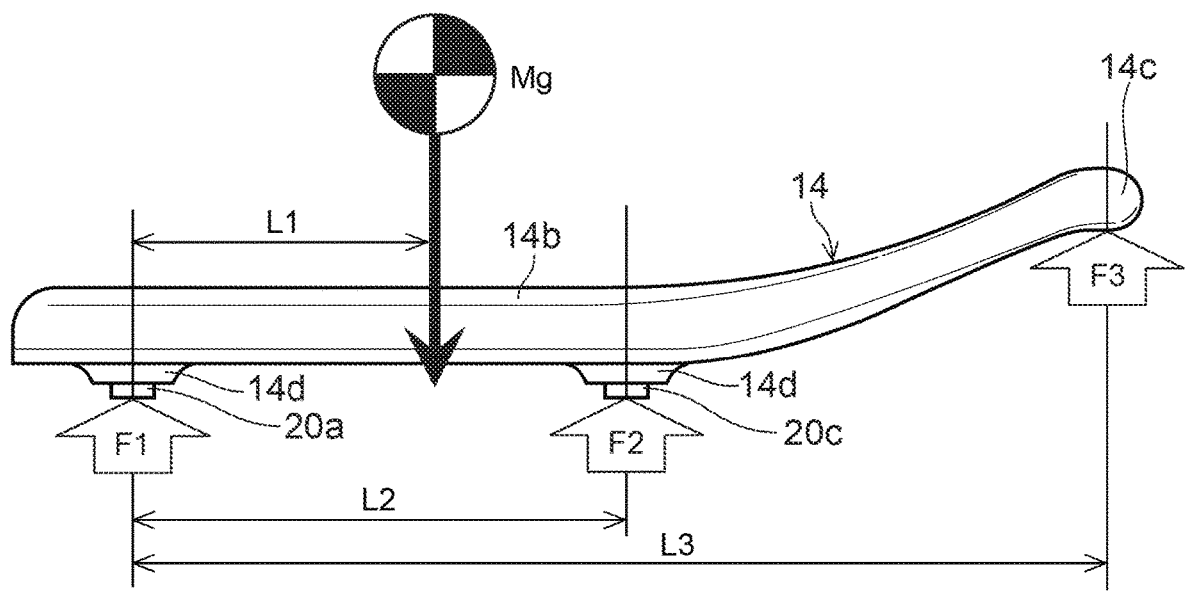
FIG. 14 is a descriptive view schematically illustrating an example of a method for calculating the estimated value.
Figure 15:
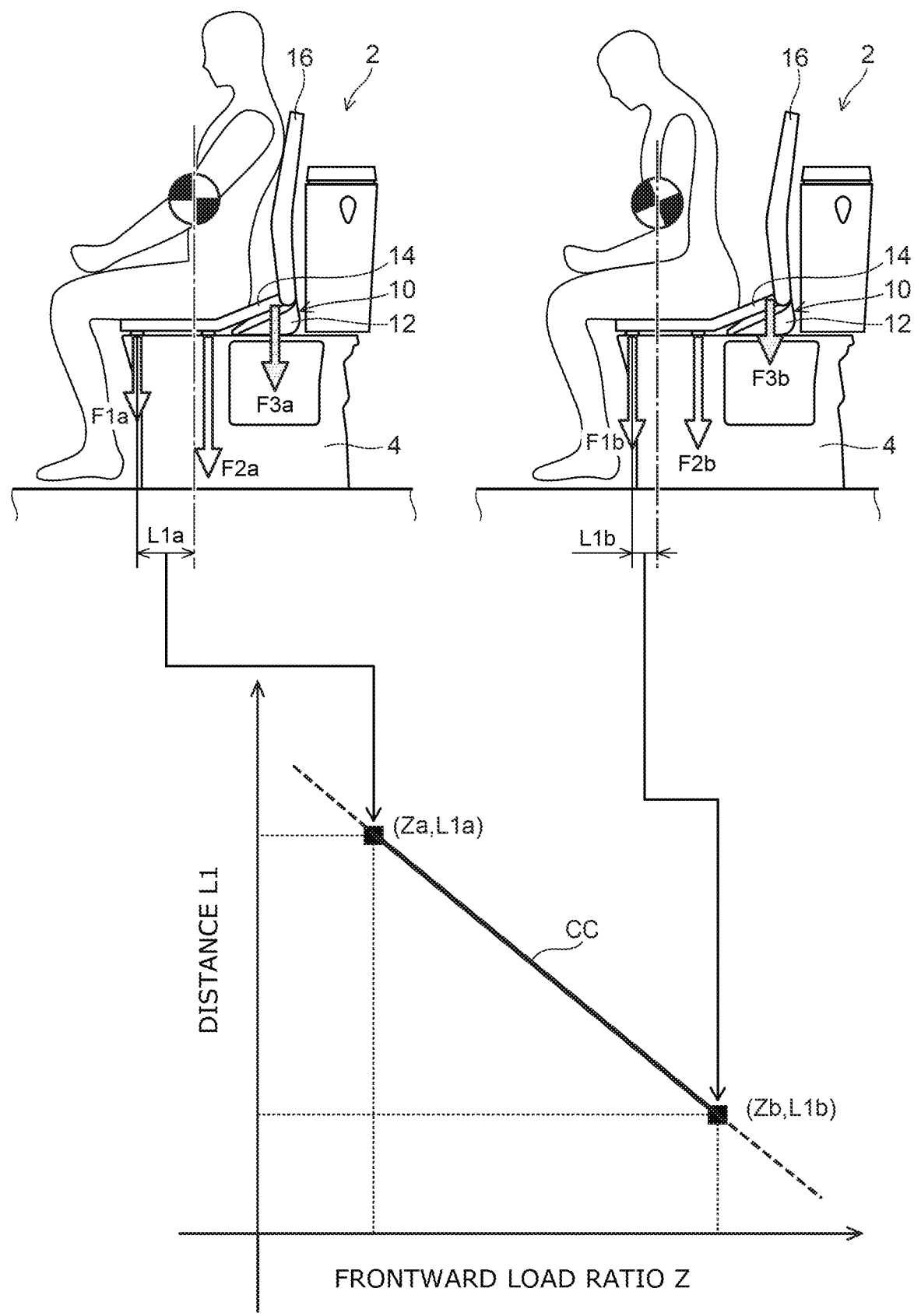
FIG. 15 is a descriptive view schematically illustrating an example of a method for calculating the estimated value.

FIG. 14 and FIG. 15 are descriptive views schematically illustrating an example of a method for calculating the estimated value.

In FIG. 14, Mg is the total body weight of the user seated on the toilet seat 14; F1 is the load supported by the load sensors 20a and 20b at the front; F2 is the load supported by the load sensors 20c and 20d at the rear; F3 is the load supported by the rotation shaft part 14c of the toilet seat 14; L1 is the distance in the frontward/rearward direction from the load sensors 20a and 20b at the front to the center of gravity of the body weight; L2 is the distance in the frontward/rearward direction from the load sensors 20a and 20b at the front to the load sensors 20c and 20d at the rear; and L3 is the distance in the frontward/rearward direction from the load sensors 20a and 20b at the front to the rotation shaft part 14c of the toilet seat 14.

Among the items recited above, the loads F1 and F2 are acquirable by the load sensors 20a to 20d. The distances L2 and L3 are acquirable by measuring the toilet seat 14. As described above, the total body weight Mg (the first load value) is acquired in the total body weight acquisition process in the register mode. On the other hand, the load F3 and the distance L1 are unknown variables.

The total body weight Mg can be represented by the following Formula (1).

$$Mg = F1 + F2 + F3 \quad (1)$$

Also, the balance of the moment around the load sensors 20a and 20b at the front can be represented by the following Formula (2).

$$Mg \times L1 = F2 \times L2 + F3 \times L3 \quad (2)$$

From Formula (1) and Formula (2) recited above, the distance L1 can be represented by the following Formula (3).

$$L1 = (F2 \times L2 + (Mg - F1 - F2) \times L3)/Mg \quad (3)$$

Based on the multiple second load values and the first load value in the total body weight estimated value acquisition process, from Formula (3) recited above, the controller 30 acquires the distance L1 (hereinbelow, called a distance L1a) when in the first seated posture and the distance L1 (hereinbelow, called a distance L1b) when in the second seated posture as multiple estimated values.

Also, the condition (the seated posture) of the forward tilt and the rearward tilt of the user can be determined using the ratio of the load F1 of the load sensors 20a and 20b at the front and the load F2 of the load sensors 20c and 20d at the rear. The posture measurement part 40 determines a frontward load ratio Z represented by the following Formula (4) to be the seated posture.

$$Z = F1/(F1 + F2) \quad (4)$$

Based on the multiple second load values, the posture measurement part 40 determines the frontward load ratio Z when in the first seated posture (hereinbelow, called a frontward load ratio Za) and the frontward load ratio Z when in the second seated posture (hereinbelow, called a frontward load ratio Zb) from Formula (4) recited above.

In the total body weight estimated value acquisition process, the controller 30 determines the distance L1a and L1b as multiple estimated values and determines the frontward load ratio Za and Zb as multiple estimated values.

Further, as illustrated in FIG. 15, the controller 30 determines a calibration curve CC of the relationship between the frontward load ratio Z and the distance L1 based on the distance L1a and L1b and the frontward load ratio Za and Zb that are determined. In the register mode, the controller 30 determines the calibration curve CC recited above each time the user is registered in the user registration process.

In the example, in the seated load measurement process of the normal-use mode (e.g., step S306 of FIG. 8), the controller 30 causes the user seated on the toilet seat 14 to form a posture having the feet away from the floor. In the seated load measurement process of the example, the controller 30 measures the third load value relating to the seated loads detected by the load sensors 20a to 20d in the state in which the user is seated on the toilet seat 14 with the feet away from the floor, and causes the posture measurement part 40 to measure the frontward load ratio Z as the seated posture.

Then, in the total body weight estimation process of the example (e.g., step S307 of FIG. 8), the total body weight estimator 42 estimates the total body weight of the user based on the third load value, the multiple command values, and the seated posture of the user measured by the posture measurement part 40.

The total body weight estimator 42 reads, from the memory 32, the multiple estimated values of the user identified in the user identification process (e.g., step S301 of FIG. 8) and determines the calibration curve CC of the user from the multiple estimated values.

Subsequently, the total body weight estimator 42 determines the distance L1 corresponding to the seated posture of the user in the seated load measurement process of the normal-use mode based on the frontward load ratio Z and the calibration curve CC measured by the posture measurement part 40.

After determining the distance L1 in the seated load measurement process, the total body weight estimator 42 estimates the load F3 applied to the rotation shaft part 14c of the toilet seat 14 from the following Formula (5) calculated from Formula (1) and Formula (2) recited above.

$$F3=(F2 \times L2 - F1 \times L1 - F2 \times L1)/(L1-L3) \quad (5)$$

Then, the total body weight estimator 42 estimates the fourth load value relating to the total body weight of the user from Formula (1) recited above.

Thus, in the register mode of the example, the multiple estimated values for estimating the total body weight are determined and stored based on the total body weight and the seated loads for each of the multiple seated postures of the user; therefore, the load that is dispersed in the rotation shaft part 14c can be estimated by considering the seated posture of the user; and a more accurate total body weight can be estimated.

In the seated load measurement process (the second process) of the example, the estimated values are acquired based on the two postures of the first seated posture and the second seated posture. The estimated values of three or more seated postures may be acquired in the seated load measurement process. In such a case, the calibration curve CC may be a curve based on the multiple estimated values or may be a straight-line approximation based on the multiple estimated values. The number of seated postures (the number of estimated values acquired) in the seated load measurement process may be any number for which at least a linear calibration curve CC can be generated.

Figure 16:
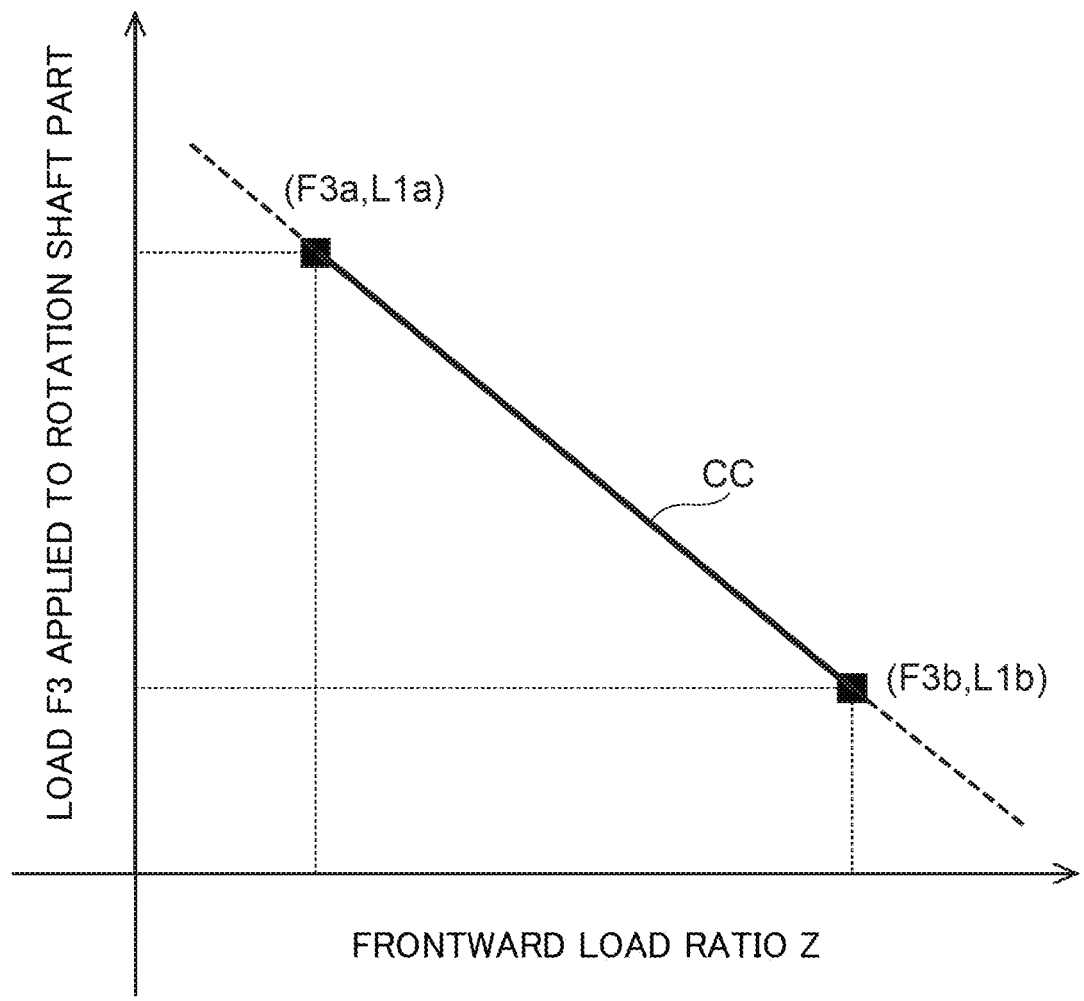
FIG. 16 is a descriptive view schematically illustrating a modification of the method for calculating the estimated value.

FIG. 16 is a descriptive view schematically illustrating a modification of the method for calculating the estimated value.

In the example illustrated in FIG. 15, in the total body weight estimated value acquisition process, the multiple estimated values of the distance L1a when in the first seated posture and the distance L1b when in the second seated posture are acquired; and the calibration curve CC of the relationship between the frontward load ratio Z and the distance L1 is determined based on the distance L1a and L1b and the frontward load ratio Za and Zb.

This is not limited thereto; in the total body weight estimated value acquisition process as illustrated in FIG. 16, a load F3a of the rotation shaft part 14c when in the first seated posture and a load F3b of the rotation shaft part 14c when in the second seated posture may be acquired as the multiple estimated values; and the calibration curve CC of the relationship between the frontward load ratio Z and the load F3 may be determined based on the load F3a and F3b and the frontward load ratio Za and Zb.

The load F3a and F3b can be determined by Formula (1) recited above. In the normal-use mode, the load F3 that corresponds to the seated posture of the user in the seated load measurement process of the normal-use mode is determined based on the calibration curve CC and the frontward load ratio Z measured by the posture measurement part 40. Thereby, the fourth load value relating to the total body weight of the user can be estimated using Formula (1) recited above. Accordingly, similarly to the embodiment, the load that is dispersed in the rotation shaft part 14c can be estimated by considering the seated posture of the user; and a more accurate total body weight can be estimated.

Embodiments of the invention are described above. However, the invention is not limited to these descriptions. Appropriate design modifications by one skilled in the art relating to the embodiments described above also are within the scope of the invention to the extent that the spirit of the invention is included. For example, the configurations, dimensions, material properties, arrangements, mounting methods, etc., of the components included in the toilet seat device 10 are not limited to those illustrated and can be modified appropriately.

The components included in the embodiments described above can be combined within the extent of technical feasibility; and such combinations are within the scope of the invention to the extent that the spirit of the invention is included.

What is claimed is:

1. A toilet seat device, comprising:
    a main part;
    a toilet seat pivotally supported to be rotatable with respect to the main part, the toilet seat including a seating part and a support leg part, the seating part being where a user is seated, the support leg part supporting a load applied to the seating part;
    a load sensor provided in the support leg part, the load sensor detecting the load applied to the support leg part;
    a controller performing at least a body weight measurement of the user based on a detection result of the load sensor; and
    a memory,
    the controller including a register mode and a normal-use mode in the body weight measurement,
    the register mode including a first process of acquiring a first load value relating to a total body weight of the user, a second process of measuring a second load value relating to a seated load detected by the load sensor in a state in which the user is seated on the toilet seat, and a third process of determining an estimated value based on the first load value and the second load value and storing the estimated value in the memory, the estimated value being for estimating the total body weight of the user from the seated load, the normal-use mode including a fourth process of measuring a third load value relating to the seated load detected by the load sensor in the state in which the user is seated on the toilet seat, and a fifth process of estimating a fourth load value relating to the total body weight of the user based on the estimated value and the third load value.

2. The device according to claim 1, further comprising a posture measurement part measuring a seated posture of the user seated on the toilet seat, the second process measuring a plurality of the second load values relating to the seated loads for each of a plurality of the seated postures detected by the load sensor and the posture measurement part for a state in which the user is seated on the toilet seat and changes the seated posture, the third process determining a plurality of the estimated values based on the first load value and the plurality of second load values and storing the plurality of estimated values in the memory, the plurality of estimated values being for estimating the total body weight of the user from the seated loads of each of the plurality of seated postures, the fourth process measuring the seated posture detected by the posture measurement part and the third load value relating to the seated load detected by the load sensor in the state in which the user is seated on the toilet seat, the fifth process estimating the fourth load value relating to the total body weight of the user based on the plurality of estimated values, the third load value, and the seated posture measured in the fourth process.

3. The device according to claim 2, wherein a plurality of the load sensors is provided, and the posture measurement part measures the seated posture based on a load distribution of the plurality of load sensors.

4. The device according to claim 3, wherein at least one of the plurality of load sensors is provided at a front of the toilet seat, an other at least one of the plurality of load sensors is provided at a rear of the toilet seat, and the posture measurement part measures the seated posture according to a ratio of a detected value of the at least one of the load sensors provided at the front and a detected value of the other at least one of the load sensors provided at the rear.

5. The device according to claim 1, further comprising a user identifier identifying the user, the controller performing at least an operation of the register mode each time the user is identified, the memory storing the estimated value each time the user is identified, the controller using the estimated value of each time the user is identified in the normal-use mode.

6. The device according to claim 1, wherein the controller is configured to update the estimated value by re-performing an operation of the register mode after performing the operation of the register mode.

7. The device according to claim 1, further comprising an operation part configured to command the controller to perform an operation of the register mode, the controller being configured to perform the operation of the register mode at any timing corresponding to an operation of the operation part.

8. The device according to claim 1, wherein in the case where a prescribed condition is satisfied, the controller automatically performs an operation of the register mode.

9. The device according to claim 7, further comprising a notification part performing at least a prescribed notification, in the case where a prescribed condition is satisfied, the controller notifying, from the notification part, that the operation of the register mode is performed.

10. The device according to claim 9, further comprising a timer measuring a time elapsed from performing the operation of the register mode, in the case where the time measured by the timer is not less than a prescribed period of time, the controller determining that the prescribed condition is satisfied.

11. The device according to claim 9, further comprising a counter counting a number of operations of the normal-use mode performed after the operation of the register mode is performed, in the case where the number counted by the counter is not less than a prescribed number, the controller determining that the prescribed condition is satisfied.

12. The device according to claim 9, wherein the controller stores the first load value in the memory in the first process, and determines that the prescribed condition is satisfied in the case where the fourth load value estimated in the normal-use mode is different from the first load value stored in the memory by not less than a prescribed value.

13. The device according to claim 8, further comprising a timer measuring a time elapsed from performing the operation of the register mode, in the case where the time measured by the timer is not less than a prescribed period of time, the controller determining that the prescribed condition is satisfied.

14. The device according to claim 8, further comprising a counter counting a number of operations of the normal-use mode performed after the operation of the register mode is performed, in the case where the number counted by the counter is not less than a prescribed number, the controller determining that the prescribed condition is satisfied.

15. The device according to claim 8, wherein the controller stores the first load value in the memory in the first process, and determines that the prescribed condition is satisfied in the case where the fourth load value estimated in the normal-use mode is different from the first load value stored in the memory by not less than a prescribed value.

16. The device according to claim 1, further comprising a notification part performing at least a prescribed notification, the controller storing the fourth load value estimated in the normal-use mode in the memory, and performing a notification from the notification part in the case where the estimated fourth load value is different, by not less than a prescribed value, from the fourth load value of a previous time stored in the memory.

* * * * *